US010836809B2

(12) United States Patent
Mwangi et al.

(10) Patent No.: US 10,836,809 B2
(45) Date of Patent: Nov. 17, 2020

(54) MOSAIC CHIMERIC VIRAL VACCINE PARTICLE

(71) Applicant: The Texas A&M University System, College Station, TX (US)

(72) Inventors: Waithaka Mwangi, College Station, TX (US); Surya Waghela, College Station, TX (US); Luc Berghman, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/516,473

(22) Filed: Jul. 19, 2019

(65) Prior Publication Data

US 2020/0079838 A1 Mar. 12, 2020

Related U.S. Application Data

(63) Continuation of application No. 15/718,385, filed on Sep. 28, 2017, now Pat. No. 10,407,491, which is a continuation of application No. 14/024,019, filed on Sep. 11, 2013, now abandoned.

(60) Provisional application No. 61/699,563, filed on Sep. 11, 2012.

(51) Int. Cl.
| | |
|---|---|
| *C07K 16/08* | (2006.01) |
| *C07K 16/28* | (2006.01) |
| *C07K 16/10* | (2006.01) |
| *A61K 35/761* | (2015.01) |
| *A61K 39/42* | (2006.01) |
| *A61K 39/00* | (2006.01) |

(52) U.S. Cl.
CPC .......... *C07K 16/081* (2013.01); *A61K 35/761* (2013.01); *A61K 39/42* (2013.01); *C07K 16/1081* (2013.01); *C07K 16/2851* (2013.01); *A61K 2039/55522* (2013.01); *C07K 2317/31* (2013.01); *C07K 2317/622* (2013.01); *C07K 2317/626* (2013.01); *C07K 2317/76* (2013.01); *C12N 2710/10343* (2013.01); *C12N 2770/24334* (2013.01); *C12N 2810/855* (2013.01)

(58) Field of Classification Search
None
See application file for complete search history.

(56) References Cited

U.S. PATENT DOCUMENTS

| | | | | |
|---|---|---|---|---|
| 6,001,613 A | 12/1999 | Donis et al. | 435/91.4 |
| 10,407,491 B2 * | 9/2019 | Mwangi | C07K 16/2851 |
| 2009/0060910 A1 | 3/2009 | Johnson et al. | 424/133.1 |
| 2014/0079704 A1 | 3/2014 | Mwangi et al. | 424/136.1 |
| 2018/0094046 A1 | 4/2018 | Mwangi | 424/186.1 |
| 2020/0079838 A1 * | 3/2020 | Mwangi | C07K 16/1081 |

FOREIGN PATENT DOCUMENTS

| | | |
|---|---|---|
| WO | WO/2008/098145 | 8/2008 |
| WO | WO/2012/038454 | 3/2012 |

OTHER PUBLICATIONS

Zimmerman et al. (JAVMA. 2006; 228 (11): 1757-1761).*
"Fort Dodge Animal Health Care Products," [http://www.wyeth.com/animalhealth].
"Novartis Animal Health," [http://www.ah.novartis.com/aqua/en/index.shtml].
"Memorial Sloan Kettering Cancer Center," [http://www.mskcc.org/mskcc/html/52438.cfm].
Akbari, O. et al. (1999) "DNA vaccination: transfection and activation of dendritic cells as key events for immunity," *Journal of Experimental Medicine* 189(1), 169-178.
Al-Haddawi, M. et al. (2007) "Impairment of innate immune responses of airway epithelium by infection with bovine viral diarrhea virus," *Veterinary Immunology and Immunopathology* 116(3-4), 153-162.
Albert, M. L. et al. (1998) "Immature dendritic cells phagocytose apoptotic cells via alphavbeta5 and CD36, and cross-present antigens to cytotoxic T lymphocytes," *Journal of Experimental Medicine* 188(7), 1359-1368.
Allred, D. R. et al. (1990) "Molecular basis for surface antigen size polymorphisms and conservation of a neutralization-sensitive epitope in *Anaplasma marginale," Proceedings of the National Academy of Sciences of the United States of America* 87(8), 3220-3224.
Armengol, E. et al. (2002) "Identification of T-cell epitopes in the structural and non-structural proteins of classical swine fever virus," *Journal of General Virology* 83(3), 551-560.
Baker, J. C. (1995) "The clinical manifestations of bovine viral diarrhea infection," *Veterinary Clinics of North America. Food Animal Practice* 11, 425-445.
Banchereau, J. et al. (1998) "Dendritic cells and the control of immunity," *Nature* 392(6673), 245-252.

(Continued)

*Primary Examiner* — Shanon A. Foley
(74) *Attorney, Agent, or Firm* — Medlen & Carroll, LLP

(57) ABSTRACT

The present invention describes compositions and methods for priming protective immunity in the presence of pre-existing maternal antibody. In some embodiments, the invention contemplates simultaneously masking vaccines to avoid antibody neutralization while targeting those vaccines to specific cell types in order to elicit an enhanced immune response. In other embodiments, vectors that recruit and activate specific antigen-presenting cells may further enhance the efficacy of those immune responses.

23 Claims, 13 Drawing Sheets

Specification includes a Sequence Listing.

(56) References Cited

OTHER PUBLICATIONS

Barbet, A. F. et al. (1987) "Characterization of an immunoprotective protein complex of Anaplasma marginale by cloning and expression of the gene coding for polypeptide Am105L," *Infection and Immunity* 55(10), 2428-2435.

Barouch, D. H. et al. (2002) "Potent CD4+ T cell responses elicited by a bicistronic Hiv-1 DNA vaccine expressing gp120 and GM-CSF," *Journal of Immunology* 168(2), 562-568.

Beer, M. et al. (2000) "A new inactivated BVDV genotype I and II vaccine: An immunisation and challenge study with BVDV genotype I," *Veterinary Microbiology* 77(1-2), 195-208.

Beer, M. et al. (1997) "Cytotoxic T-lymphocyte responses in cattle infected with BVDV," *Veterinary Microbiology* 58, 9-22.

Bennett, C. L. et al. (2007) "Langerhans cells are required for efficient presentation of topically applied hapten to T cells," *Journal of Immunology* 179(10), 6830-6835.

Biragyn, A. et al. (2001) "Mediators of innate immunity that target immature, but not mature, dendritic cells induce antitumor immunity when genetically fused with nonimmunogenic tumor antigens," *Journal of Immunology* 167, 6644-6653.

Blue, C. E. et al. (2004) "The relevance of complement to virus biology," *Virology* 319(2), 176-184.

Bolin, S. R. (1993) "Immunogens of bovine viral diarrhea virus," *Veterinary Microbiology* 37(3-4), 263-271.

Bonifaz, L. et al. (2002) "Efficient targeting of protein antigen to the dendritic cell receptor DEC-205 in the steady state leads to antigen presentation on major histocompatibility complex class I products and peripheral CD8+ T cell tolerance," *Journal of Experimental Medicine* 196(12), 1627-1638.

Bonifaz, L. C. et al. (2004) "In vivo targeting of antigens to maturing dendritic cells via the DEC-205 receptor improves T cell vaccination," *Journal of Experimental Medicine* 199(6), 815-824.

Bozzacco, L. et al. (2007) "DEC-205 receptor on dendritic cells mediates presentation of HIV gag protein to CD8+ T cells in a spectrum of human MHC I haplotypes," *Proceedings of the National Academy of Sciences of the United States of America* 104(4), 1289-1294.

Brar, J. S. et al. (1978) "Maternal immunity to infectious bovine rhinotracheitis and bovine viral diarrhea viruses: duration and effect on vaccination in young calves," *American Journal of Veterinary Research* 39(2), 241-244.

Brown, W. C., G. H. Palmer, H. A. Lewin, and T. C. McGuire. (2001) "CD4+ T lymphocytes from calves immunized with *Anaplasma marginale* Major Surface Protein 1 (MSP1), a heteromeric complex of MSP1a and MSP1b, preferentially recognize the MSP1a carboxyl terminus that is conserved among strains," *Infection and Immunity* 69(11), 6853-6862.

Brown, W. C. et al. (2002) "Major histocompatibility complex class II DR-restricted memory CD4+ T lymphocytes recognize conserved immunodominant epitopes of *Anaplasma marginale* major surface protein 1a," *Infection and Immunity* 70(10), 5521-5532.

Campbell, J. R. (2004) "Effect of bovine viral diarrhea virus in the feedlot," *Veterinary Clinics of North America. Food Animal Practice* 20(1), 39-50.

Casares, S. et al. (1997) "Antigen presentation by dendritic cells after immunization with DNA encoding a major histocompatibility complex class II-restricted viral epitope," *Journal of Experimental Medicine* 186(9), 1481-1486.

Chen, H.-W. et al. (2002) "Linkage of CD40L to a self-tumor antigen enhances the antitumor immune responses of dendritic cell-based treatment," *Cancer Immunology Immunotherapy* 51(6), 341-348.

Cheong, C. et al. (2010) "Improved cellular and humoral immune responses in vivo following targeting of HIV Gag to dendritic cells within human anti-human DEC205 monoclonal antibody," *Blood* 116(19), 3828-3838.

Collen, T. et al. (2002) "Analysis of the repertoire of cattle CD4(+) T cells reactive with bovine viral diarrhoea virus," *Veterinary Immunology and Immunopathology* 87(3-4), 235-238.

Collen, T. et al. (2000) "CD4(+) T-cell responses to bovine viral diarrhoea virus in cattle," *Virus Research* 67(1), 67-80.

Collett, M. S. et al. (1988) "Proteins encoded by bovine viral diarrhea virus: the genomic organization of a pestivirus," *Virology* 165(1), 200-208.

Collett, M. S. et al. (1991) "Bovine viral diarrhea virus genomic organization," *Archives of Virology. Supplementum 3*, 19-27.

Condon, C. et al. (1996) "DNA-based immunization by in vivo transfection of dendritic cells," *Nature Medicine* 2(10), 1122-1128.

Correale, P., G. Campoccia., K. Y. Tsang., L. Micheli., M. G. Cusi., M. Sabatino., G. Bruni., S. Sestini., R. Petrioli., D. Pozzssere., et al . . . (2001) "Recruitment of dendritic cells and enhanced antigen-specific immune reactivity in cancer patients treated with hr-GM-CSF (molgramostim) and hr-IL-2: results from a phase 1b clinical trial," *European Journal of Cancer* 37(7), 892-902.

Cortese, V. S. et al. (1998) "Clinical and immunologic responses of vaccinated and unvaccinated calves to infection with a virulent type-II isolate of bovine viral diarrhea virus," *Journal of the American Veterinary Medical Association* 213(9), 1312-1319.

Dani, A. et al. (2004) "The pathway for MHCII-mediated presentation of endogenous proteins involves peptide transport to the endo-lysosomal compartment," *Journal of Cell Science* 117(Pt 18), 4219-4230.

Demangel, C. et al. (2005) "Single chain antibody fragments for the selective targeting of antigens to dendritic cells," *Molecular Immunology* 42(8), 979-985.

Demotz, S. et al. (1990) "The minimal number of class II MHC-antigen complexes needed for T cell activation," *Science* 249(4972), 1028-1030.

Deng, R. et al. (1992) "Molecular cloning and nucleotide sequence of a pestivirus genome, noncytopathic bovine viral diarrhea virus strain SD-1," *Virology* 191(2), 867-869.

Deregt, D. et al. (1998) "Mapping of a type 1-specific and a type-common epitope on the E2 (gp53) protein of bovine viral diarrhea virus with neutralization escape mutants," *Virus Research* 53(1), 81-90.

Deregt, D. et al. (2005) "Mapping of two antigenic domains on the NS3 protein of the pestivirus bovine viral diarrhea virus," *Veterinary Microbiology* 108(1-2), 13-22.

Descoteaux, L. et al. (2003) "Comparison of humoral immune responses in dairy heifers vaccinated with 3 different commercial vaccines against bovine viral diarrhea virus and bovine herpesvirus-1," *Canadian Veterinary Journal* 44(10), 816-821.

Donis, R. O. (1995) "Molecular biology of bovine viral diarrhea virus and its interactions with the host," *Veterinary Clinics of North America. Food Animal Practice* 11(3), 393-423.

Donis, R. O. et al. (1988) "Neutralizing monoclonal antibodies to bovine viral diarrhoea virus bind to the 56K to 58K glycoprotein," *Journal of General Virology* 69 ( Pt 1), 77-86.

Donnelly, J. J. et al. (1995) "Preclinical efficacy of a prototype DNA vaccine: enhanced protection against antigenic drift in influenza virus," *Nature Medicine* 1(6), 583-587.

Duval, M. et al. (2008) "A Bispecific Antibody Composed of a Nonneutralizing Antibody to the gp41 Immunodominant Region and an Anti-CD89 Antibody Directs Broad Human Immunodeficiency Virus Destruction by Neutrophils," *Journal of Virology* 82(9), 4671-4674.

Edwards, C. P. et al. (1993) "Current applications of COS cell based transient expression systems," *Current Opinion in Biotechnology* 4(5), 558-563.

Elahi, S. M. et al. (1999) "Recombinant adenoviruses expressing the E2 protein of bovine viral diarrhea virus induce humoral and cellular immune responses," *FEMS Microbiology Letters* 177(1), 159-166.

Elahi, S. M. et al. (1999) "Induction of humoral and cellular immune responses against the nucleocapsid of bovine viral diarrhea virus by an adenovirus vector with an inducible promoter," *Virology* 261(1), 1-7.

Esser, M. T. et al. (2003) "Memory T cells and vaccines," *Vaccine* 21(5-6), 419-430.

(56) References Cited

OTHER PUBLICATIONS

Feltquate, D. M. et al. (1997) "Different T helper cell types and antibody isotypes generated by saline and gene gun DNA immunization," *Journal of Immunology* 158(5), 2278-2284.

Ficken, M. D. et al. (2006) "Effects of modified-live bovine viral diarrhea virus vaccines containing either type 1 or types 1 and 2 BVDV on heifers and their offspring after challenge with noncytopathic type 2 BVDV during gestation," *Journal of the American Veterinary Medical Association* 228(10), 1559-1564.

Fujii, S., K. Liu, C. Smith, A. J. Bonito, and R. M. Steinman. (2004) "The linkage of innate to adaptive immunity via maturing dendritic cells in vivo requires CD40 ligation in addition to antigen presentation and CD80/86 co-stimulation," *Journal of Experimental Medicine* 199, 1607-1618.

Fulton, R. W. et al. (2004) "Maternally derived humoral immunity to bovine viral diarrhea virus (BVDV) 1a, BVDV 1b, BVDV2, bovine herpesvirus-1, parainfluenza-3 virus bovine respiratory syncytial virus, Mannheimia haemolytica and Pasteurella multocida in beef calves, antibody decline by half-life studies and effect on response to vaccination," *Vaccine* 22(5-6), 643-649.

Fulton, R. W. et al. (2000) "Bovine viral diarrhea virus types 1 and 2 antibody response in calves receiving modified live virus or inactivated vaccines," *Vaccine* 19(2), 264-274.

Fulton, R. W. et al. (2006) "Evaluation of diagnostic tests used for detection of bovine viral diarrhea virus and prevalence of subtypes 1a, 1b, and 2a in persistently infected cattle entering a feedlot," *Journal of the American Veterinary Medical Association* 228(4), 578-584.

Fulton, R. W. et al. (2005) "Bovine viral diarrhoea virus (BVDV) subgenotypes in diagnostic laboratory accessions: distribution of BVDV1a, 1b, and 2a subgenotypes," *Veterinary Microbiology* 111(1-2), 35-40.

Gallucci, S. et al. (1999) "Natural adjuvants: endogenous activators of dendritic cells," *Nature Medicine* 5(11), 1249-1255.

Galvin, T. A. et al. (2000) "Effect of different promoters on immune responses elicited by HIV-1 gag/env multigenic DNA vaccine in Macaca mulatta and Macaca nemestrina," *Vaccine* 18(23), 2566-2583.

Gares, S. L. et al. (2006) "Immunotargeting with CD154 (CD40 ligand) enhances DNA vaccine responses in ducks," *Clinical and Vaccine Immunology* 13(8), 958-965.

Gill, N. et al. (2006) "Induction of innate immunity against herpes simplex virus type 2 infection via local delivery of Toll-like receptor ligands correlates with beta interferon production," *Journal of Virology* 80(20), 9943-9950.

Glew, E. J. et al. (2003) "Differential effects of bovine viral diarrhoea virus on monocytes and dendritic cells," *Journal of General Virology* 84(7), 1771-1780.

Gliddon, D. R. et al. (2004) "DEC-205 expression on migrating dendritic cells in afferent lymph," *Immunology* 111(3), 262-272.

Gogev, S. et al. (2002) "Induction of protective immunity to bovine herpesvirus type 1 in cattle by intranasal administration of replication-defective human adenovirus type 5 expressing glycoprotein gC or gD," *Vaccine* 20(9-10), 1451-1465.

Granelli-Piperno, A. et al. (2005) "Dendritic Cell-Specific Intercellular Adhesion Molecule 3-Grabbing Nonintegrin/CD209 Is Abundant on Macrophages in the Normal Human Lymph Node and Is Not Required for Dendritic Cell Stimulation of the Mixed Leukocyte Reaction," *Journal of Immunology* 175(7), 4265-4273.

Grossmann, C. et al. (2009) "Enhancement of the priming efficacy of DNA vaccines encoding dendritic cell-targeted antigens by synergistic toll-like receptor ligands," *BMC Immunology* 10(1), 43.

Gurer, C. et al. (2008) "Targeting the nuclear antigen 1 of Epstein-Barr virus to the human endocytic receptor DEC-205 stimulates protective T-cell responses," *Blood* 112(4), 1231-1239.

Haase, C. et al. (2004) "CD40 is necessary for activation of naive T cells by a dendritic cell line in vivo but not in vitro," *Scandinavian Journal of Immunology* 59, 237-245.

Haddad, D., J. et al. (2000) "Plasmid vaccine expressing granulocyte-macrophage colony-stimulating factor attracts infiltrates including immature dendritic cells into injected muscles," *Journal of Immunology* 165, 3772-3781.

Haisma, H. J. et al. (2000) "Targeting of adenoviral vectors through a bispecific single-chain antibody," *Cancer Gene Therapy* 7, 901-904.

Hamers, C. et al. (2001) "Diversity Among Bovine Pestiviruses," *Veterinary Journal* 161(2), 112-122.

Han, S. et al. (2008) "Rapid deletion of antigen-specific CD4+ T cells following infection represents a strategy of immune evasion and persistence for Anaplasma marginate," *Journal of Immunology* 181(11), 7759-7769.

Harding, C. V. et al. (1990) "Quantitation of antigen-presenting cell MHC class II/peptide complexes necessary for T-cell stimulation," *Nature* 346(6284), 574-576.

Hegde, N. R. et al. (1997) "The use of bovine MHC class I allele-specific peptide motifs and proteolytic cleavage specificities for the prediction of potential cytotoxic T lymphocyte epitopes of bovine viral diarrhea virus," *Virus Genes* 14(2), 111-121.

Holliger, P. et al. (2005) "Engineered antibody fragments and the rise of single domains," *Nature Biotechnology* 23(9), 1126-1136.

Hotta, C. et al. (2006) "The delivery of an antigen from the endocytic compartment into the cytosol for cross-presentation is restricted to early immature dendritic cells," *Immunology* 117(1), 97-107.

Howard, C. J. et al. (1989) "Protection against respiratory infection with bovine viral diarrhoea virus by passively acquired antibody," *Veterinary Microbiology* 19, 195-203.

Howard, C. J. et al. (1992) "Immunity to bovine viral diarrhoea virus in calves: the role of different T cell subpopulations analysed by specific depletion in vivo with monoclonal antibodies," *Veterinary Immunology and Immunopathology* 32, 303-314.

Huang, H. I. et al. (2004) "Improved immunogenicity of a self tumor antigen by covalent linkage to CD40 ligand," *International Journal of Cancer* 108(5), 696-703.

Idoyaga, J. et al. (2011) "Comparable T helper 1 (THL) and CD8 T-cell immunity by targeting HIV gag p24 to CD8 dendritic cells within antibodies to Langerin, DEC205, and Clec9A," *Proceedings of the National Academy of Sciences of the United States of America* 108(6), 2384-2389.

Jechlinger, W. (2006) "Optimization and delivery of plasmid DNA for vaccination," *Expert Review of Vaccines* 5(6), 803-825.

Jiang, W. et al. (1995) "The receptor DEC-205 expressed by dendritic cells and thymic epithelial cells is involved in antigen processing," *Nature* 375, 151-155.

Johnson, T. S. et al. (2008) "Inhibition of Melanoma Growth by Targeting of Antigen to Dendritic Cells via an Anti-DEC-205 Single-Chain Fragment Variable Molecule," *Clinical Cancer Research* 14(24), 8169-8177.

Kamen, A. et al. (2004) "Development and optimization of an adenovirus production process," *Journal of Gene Medicine* 6(S1), S184-S192.

Kelling, C. L. (2004) "Evolution of bovine viral diarrhea virus vaccines," *Veterinary Clinics of North America. Food Animal Practice* 20(1), 115-129.

Kennedy, J. A. (2006) "Diagnostic efficacy of a reverse transcriptase-polymerase chain reaction assay to screen cattle for persistent bovine viral diarrhea virus infection," *Journal of the American Veterinary Medical Association* 229(9), 1472-1474.

Kissenpfennig, A. et al. (2006) "Langerhans cells—revisiting the paradigm using genetically engineered mice," *Trends in Immunology* 27(3), 132-139.

Klechevsky, E. et al. (2006) "Interstitial dendritic cells and Langerhans cells differentially prime humoral and cellular immunity.," *Journal of Immunology* 176(Supplemental), S59.

Koch, F. et al. (1996) "High level IL-12 production by murine dendritic cells: upregulation via MHC class II and CD40 molecules and downregulation by IL-4 and IL-10," *Journal of Experimental Medicine* 184(2), 741-746.

Köhler, G. et al. (1976) "Fusion between immunoglobulin-secreting and nonsecreting myeloma cell lines," *European Journal of Immunology* 6(4), 292-295.

(56) References Cited

OTHER PUBLICATIONS

Korn, T. et al. (2004) "Recombinant bispecific antibodies for the targeting of adenoviruses to CEA-expressing tumour cells: a comparative analysis of bacterially expressed single-chain diabody and tandem scFv," *Journal of Gene Medicine* 6(6), 642-651.

Kuttner, G. et al. (2004) "Linker peptide and affinity tag for detection and purification of single-chain Fv fragments," *BioTechniques* 36(5), 864-870.

Lanzavecchia, A. (1996) "Mechanisms of antigen uptake for presentation," *Current Opinion in Immunology* 8(3), 348-354.

Lanzavecchia, A. et al. (1992) "Irreversible association of peptides with class II MHC molecules in living cells," *Nature* 357(6375), 249-252.

Leachman, S. A. et al. (2000) "Granulocyte-macrophage colony-stimulating factor priming plus papillomavirus E6 DNA vaccination: effects on papilloma formation and regression in the cottontail rabbit papillomavirus—rabbit model," *Journal of Virology* 74(18), 8700-8708.

Lehner, P. J. et al. (1996) "Processing and delivery of peptides presented by MHC class I molecules," *Current Opinion in Immunology* 8(1), 59-67.

Li, W. (2005) "Synergistic antibody induction by antigen-CD40 ligand fusion protein as improved immunogen," *Immunology* 115(2), 215-222.

Liang, R. et al. (2006) "Priming with DNA encoding E2 and boosting with E2 protein formulated with CpG oligodeoxynucleotides induces strong immune responses and protection from Bovine viral diarrhea virus in cattle," *Journal of General Virology* 87(Pt 10), 2971-2982.

Liu, Y. et al. (2002) "Adenovirus-mediated CD40 ligand gene-engineered dendritic cells elicit enhanced CD8(+) cytotoxic T-cell activation and antitumor immunity," *Cancer Gene Therapy* 9(2), 202.

Lore, K. et al. (2003) "Toll-like receptor ligands modulate dendritic cells to augment cytomegalovirus- and HIV-1-specific T cell responses," *Journal of Immunology* 171(8), 4320-4328.

Lubeck, M. D. et al. (1994) "Immunogenicity of recombinant adenovirus-human immunodeficiency virus vaccines in chimpanzees following intranasal administration," *AIDS Research and Human Retroviruses* 10(11), 1443-1449.

Ludewig, B. et al. (1998) "Dendritic cells efficiently induce protective antiviral immunity," *Journal of Virology* 72(5), 3812-3818.

Maamary, J. et al. (2011) "Newcastle disease virus expressing a dendritic cell-targeted HIV gag protein induces a potent gag-specific immune response in mice," *Journal of Virology* 85(5), 2235-2246.

Maeda, K. et al. (2005) "Recombinant adenovirus vector vaccine induces stronger cytotoxic T-cell responses than recombinant vaccinia virus vector, plasmid DNA, or a combination of these," *Viral Immunology* 18(4), 657-667.

Manoj, S. et al. (2003) "Targeting with bovine CD154 enhances humoral immune responses induced by a DNA vaccine in sheep," *Journal of Immunology* 170(2), 989-996.

Mazzei, G. J. et al. (1995) "Recombinant soluble trimeric CD40 ligand is biologically active," *Journal of Biological Chemistry* 270 7025-7028.

McClurkin, A. W. et al. (1984) "Production of cattle immunotolerant to bovine viral diarrhea virus," *Canadian Journal of Comparative Medicine and Veterinary Science* 48(2), 156-161.

McIlhinney, R. A. (2004) "Generation and use of epitope-tagged receptors," *Methods in Molecular Biology* 259, 81-98.

Mertens, B. et al. (1995) "Cloning of two members of the TNF-superfamily in cattle: CD40 ligand and tumor necrosis factor alpha," *Immunogenetics* 42(5), 430-431.

Monteil, M. et al. (2000) "Single inoculation of replication-defective adenovirus-vectored vaccines at birth in piglets with maternal antibodies induces high level of antibodies and protection against pseudorabies," *Vaccine* 18(17), 1738-1742.

Moss, R. B. (2009) "Prospects for control of emerging infectious diseases with plasmid DNA vaccines," *Journal of Immune Based Therapies and Vaccines* 7(1), 3.

Munoz-Zanzi, C. A. et al. (2002) "Predicted ages of dairy calves when colostrum-derived bovine viral diarrhea virus antibodies would no longer offer protection against disease or interfere with vaccination," *Journal of the American Veterinary Medical Association* 221(5), 678-685.

Mwangi, W. (2012) Priming Bovine Viral Diarrhea Virus-Specific Adaptive Immunity in Neonatal Calves.

Mwangi, W. et al. (2002) "DNA-encoded fetal liver tyrosine kinase 3 ligand and granulocyte macrophage-colony-stimulating factor increase dendritic cell recruitment to the inoculation site and enhance antigen-specific CD4+ T cell responses induced by DNA vaccination of outbred animals," *Journal of Immunology* 169(7), 3837-3846.

Mwangi, W. et al. (2000) "Identification of Fetal Liver Tyrosine Kinase 3 (Flt3) Ligand Domain Required for Receptor Binding and Function Using Naturally Occurring Ligand Isoforms," *Journal of Immunology* 165(12), 6966-6974.

Mwangi, W. et al. (2007) "DNA vaccine construct incorporating intercellular trafficking and intracellular targeting motifs effectively primes and induces memory B and T cell responses in outbred animals," *Clinical and Vaccine Immunology* 14(3), 304-311.

Mwangi, W., W. C. Brown, G. A. Splitter, Y. Zhuang, K. Kegerreis, and G. H. Palmer. (2005) "Enhancement of antigen acquisition by dendritic cells and MHC class II-restricted epitope presentation to CD4+ T cells using VP22 DNA vaccine vectors that promote intercellular spreading following initial transfection," *Journal of Leukocyte Biology* 78(2), 401-411.

Nchinda, G. et al. (2008) "The efficacy of DNA vaccination is enhanced in mice by targeting the encoded protein to dendritic cells," *Journal of Clinical Investigation* 118(4), 1427-1436.

Nelson, C. A. et al. (1994) "Peptides determine the lifespan of MHC class II molecules in the antigen-presenting cell," *Nature* 371(6494), 250-252.

Njongmeta, L. et al. (2007) "Immunization of cattle with a single dose of a DNA vaccine capable of dendritic cell recruitment, antigen targeting, and activation primes and induces significant memory B and T cell responses," *In-preparation*.

Njongmeta, L. M. et al. (2012) "CD205 antigen targeting combined with dendritic cell recruitment factors and antigen-linked CD40L activation primes and expands significant antigen-specific antibody and CD4+ T cell responses following DNA vaccination of outbred animals," *Vaccine* 30(9), 1624-1635.

Nobiron, I. et al. (2003) "DNA vaccination against bovine viral diarrhoea virus induces humoral and cellular responses in cattle with evidence for protection against viral challenge," *Vaccine* 21(17-18), 2082-2092.

Norimine, J. et al. (2006) "Quantitation of Anaplasma marginate major surface protein (MSP)1a and MSP2 epitope-specific CD4 T lymphocytes using bovine DRB3*1101 and DRB3*1201 tetramers," *Immunogenetics* 58(9), 726-739.

Nussenzweig, M. C. et al. (1982) "A monoclonal antibody specific for mouse dendritic cells," *Proceedings of the National Academy of Sciences of the United States of America* 79(1), 161-165.

O'Brien, P. M. et al. (1999) "Generation of native bovine mAbs by phage display," *Proceedings of the National Academy of Sciences* 96(2), 640-645.

Öhlschläger, P. et al. (2009) "Enhancement of immunogenicity of a therapeutic cervical cancer DNA-based vaccine by co-application of sequence-optimized genetic adjuvants," *International Journal of Cancer* 125(1), 189-198.

Ott, R. L. (1992) *An introduction of statistical methods and data analysis* 4th edition ed., Duxbery, CA.

Oxenius, A. et al. (1998) "CD4+ T-cell induction and effector functions: a comparison of immunity against soluble antigens and viral infections," in *Advances in Immunology*, pp. 313-367.

Pacheco, J. M. et al. (2005) "Rapid protection of cattle from direct challenge with foot-and-mouth disease virus (FMDV) by a single inoculation with an adenovirus-vectored FMDV subunit vaccine," *Virology* 337(2), 205-209.

Palmer, G. H. et al. (1995) "Molecular basis for vaccine development against anaplasmosis and babesiosis," *Veterinary Parasitology* 57(1-3), 233-253.

(56) References Cited

OTHER PUBLICATIONS

Palmer, G. H. et al. (1999) "Molecular basis for vaccine development against the ehrlichial pathogen Anaplasma marginale," *Parasitology Today* 15(7), 281-286.
Palmer, G. H. et al. (1987) "Characterization of a neutralization-sensitive epitope on the Am 105 surface protein of *Anaplasma marginale*," *International Journal for Parasitology* 17(7), 1279-1285.
Pan, P.-Y. et al. (2004) "In situ recruitment of antigen-presenting cells by intratumoral GM-CSF gene delivery," *Cancer Immunology Immunotherapy* 53(1), 17-25.
Park, Y. H. et al. (2004) "Characterization of lymphocyte subpopulations and major histocompatibility complex haplotypes of mastitis-resistant and susceptible cows," *Journal of Veterinary Science* 5(1), 29-39.
Pauly, T. et al. (1995) "Classical swine fever virus-specific cytotoxic T lymphocytes and identification of a T cell epitope," *Journal of General Virology* 76(12), 3039-3049.
Pellerin, C. J. et al. (1994) "Identification of a new group of bovine viral diarrhea virus strains assocaieted with severe outbreaks and high mortalities," *Virology* 203, 260-268.
Polack, F. P. et al. (2000) "Successful DNA immunization against measles: neutralizing antibody against either the hemagglutinin or fusion glycoprotein protects rhesus macaques without evidence of atypical measles," *Nature Medicine* 6(7), 776-781.
Porgador, A. et al. (1998) "Predominant role for directly transfected dendritic cells in antigen presentation to CD8+ T cells after gene gun immunization," *Journal of Experimental Medicine* 188(6), 1075-1082.
Prins, R. M. et al. (2006) "The TLR-7 agonist, imiquimod, enhances dendritic cell survival and promotes tumor antigen-specific T cell priming: relation to central nervous system antitumor immunity," *Journal of Immunology* 176(1), 157-164.
Pulendran, B. et al. (2000) "Flt3-ligand and granulocyte colony-stimulating factor mobilize distinct human dendritic cell subsets in vivo," *Journal of Immunology* 165(1), 566-572.
Reber, A. J. et al. (2006) "Evaluation of multiple immune parameters after vaccination with modified live or killed bovine viral diarrhea virus vaccines," *Comparative Immunology, Microbiology and Infectious Diseases* 29(1), 61-77.
Rice, C. M. et al. (1996) "Fields Virology," in *Raven Press*, pp. 931-950, Philadelphia.
Ridpath, J. F. et al. (2015) "Comparison of the breadth and complexity of bovine viral diarrhea (BVDV) populations circulating in 34 persistently infected cattle generated in one outbreak," *Virology* 485(Supplement C), 297-304.
Ridpath, J. F. et al. (1994) "Segregation of bovine viral diarrhea virus into genotypes," *Virology* 205, 66-74.
Rosas, C. T. et al. (2007) "Evaluation of the vaccine potential of an equine herpesvirus type 1 vector expressing bovine viral diarrhea virus structural proteins," *Journal of General Virology* 88(Pt 3), 748-757.
Rowlands, G. J. et al. (2000) "A statistically derived index for classifying East Coast fever reactions in cattle challenged with Theileria parva under experimental conditions," *Parasitology* 120 (Pt 4), 371-381.
Rozis, G. et al. (2005) "Langerhans cells are more efficiently transduced than dermal dendritic cells by adenovirus vectors expressing either group C or group B fibre protein: Implications for mucosal vaccines," *European Journal of Immunology* 35(9), 2617-2626.
Rumenapf, T. et al. (1993) "Processing of the envelope glycoproteins of pestiviruses," *Journal of Virology* 67(6), 3288-3294.
Serra, P. et al. (2003) "CD40 ligation releases immature dendritic cells from the control of regulatory CD4+CD25+ T cells," *Immunity* 19(6), 877-889.
Shalaby, W. S. et al. (2004) "Absorbable microparticulate cation exchanger for immunotherapeutic delivery," *Journal of Biomedical Materials Research Part B: Applied Biomaterials* 69(2), 173-182.

Sin, J. I. et al. (2001) "Modulation of cellular responses by plasmid CD40L: CD40L plasmid vectors enhance antigen-specific helper T cell type 1 CD4+ T cell-mediated protective immunity against herpes simplex virus type 2 in vivo," *Human Gene Therapy* 12(9), 1091-1102.
Solheim, J. C. et al. (2007) "Spleen but not tumor infiltration by dendritic and T cells is increased by intravenous adenovirus-Flt3 ligand injection," *Cancer Gene Therapy* 14(4), 364-371.
Staveley-O'Carroll, K. et al. (2003) "In vivo ligation of CD40 enhances priming against the endogenous tumor antigen and promotes CD8+ T cell effector function in SV40 T antigen transgenic mice," *Journal of Immunology* 171(2), 697-707.
Steinman, R. M. (1991) "The dendritic cell system and its role in immunogenicity," *Annual Review of Immunology* 9, 271.
Steinman, R. M. (2001) "Dendritic cells and the control of immunity: enhancing the efficiency of antigen presentation," *Mount Sinai Journal of Medicine* 68(3), 160-166.
Steinman, R. M. et al. (1999) "Antigen capture, processing, and presentation by dendritic cells: recent cell biological studies," *Human Immunology* 60(7), 562-567.
Tatsis, N. E. et al. (2004) "Adenoviruses as Vaccine Vectors," *Molecular Therapy* 10(4), 616-629.
Thiel, H. J. et al. (1996) "Fields Virology," pp. 1059-1074, Raven Press, Philadelphia.
Thurmond, M. C. et al. (2001) "Effect of calfhood vaccination on transmission of bovine viral diarrhea virus under typical drylot dairy conditions," *Journal of the American Veterinary Medical Association* 219(7), 968-975.
Tripp, R. A. et al. (2000) "CD40 ligand (CD154) enhances the Th1 and antibody responses to respiratory syncytial virus in the BALB/c mouse," *Journal of Immunology* 164(11), 5913-5921.
Trumpfheller, C. et al. (2006) "Intensified and protective CD4+ T cell immunity in mice with anti-dendritic cell HIV gag fusion antibody vaccine," *Journal of Experimental Medicine* 203(3), 607-617.
Tsuji, T. et al. (2011) "Antibody-targeted NY-ESO-1 to mannose receptor or DEC-205 in vitro elicits dual human CD8+ and CD4+ T cell responses with broad antigen specificity," *Journal of Immunology* 186(2), 1218-1227.
Valitutti, S. et al. (1995) "Serial triggering of many T-cell receptors by a few peptide-MHC complexes," *Nature* 375(6527), 148-151.
Van Oirschot, J. T. et al. (1999) "Vaccination of cattle against bovine viral diarrhoea," *Veterinary Microbiology* 64(2-3), 169-183.
Wands, J. R. et al. (1975) "Serial studies of hepatitis-associated antigen and antibody in patients receiving antitumor chemotherapy for myeloproliferative and lymphoproliferative disorders," *Gastroenterology* 68(1), 105-112.
Wang, R. et al. (1998) "Induction of antigen-specific cytotoxic T lymphocytes in humans by a malaria DNA vaccine," *Science* 282(5388), 476-480.
Wang, R. et al. (2001) "Induction of CD4+ T cell-dependent CD8+ type 1 responses in humans by a malaria DNA vaccine," *Proceedings of the National Academy of Sciences of the United States of America* 98(19), 10817-10822.
Wang, R. et al. (2004) "Induction in humans of CD8+ and CD4+ T cell and antibody responses by sequential immunization with malaria DNA and recombinant protein," *Journal of Immunology* 172(9), 5561-5569.
Wang, W. W. et al. (2008) "A versatile bifunctional dendritic cell targeting vaccine vector," *Molecular Pharmaceutics* 6(1), 158-172.
Wang, W. W. et al. (2005) "Antigen targeting to dendritic cells with bispecific antibodies," *Journal of Immunological Methods* 306(1), 80-92.
Watts, C. (1997) "Capture and processing of exogenous antigens for presentation on MHC molecules," *Annual Review of Immunology* 15, 821-850.
Weiss, W. R. et al. (1998) "A plasmid encoding murine granulocyte-macrophage colony-stimulating factor increases protection conferred by a malaria DNA vaccine," *Journal of Immunology* 161(5), 2325-2332.
Williams, A. F. et al. (1977) "Analysis of cell surfaces by xenogeneic myeloma-hybrid antibodies: Differentiation antigens of rat lymphocytes," *Cell* 12(3), 663-673.

(56) References Cited

OTHER PUBLICATIONS

Wilson, I. A. et al. (1994) "Antibody-antigen interactions: new structures and new conformational changes," *Current Opinion in Structural Biology* 4(6), 857-867.

Wittum, T. E. et al. (2001) "Persistent BVDV infection in US beef herds," *Preventive Veterinary Medicine* 49(1-2), 83-94.

Wolff, J. A. et al. (1992) "Long-term persistence of plasmid DNA and foreign gene expression in mouse muscle," *Human Molecular Genetics* 1(6), 363-369.

Wolff, J. A. et al. (1990) "Direct gene transfer into mouse muscle in vivo," *Science* 247, 1465-1468.

Yamamoto, M. et al. (2003) "Transcription Initiation Activity of Adenovirus Left-End Sequence in Adenovirus Vectors with E1 Deleted," *Journal of Virology* 77(2), 1633-1637.

Yao, Q. et al. (2010) "Immunogenicity and protective efficacy of a DNA vaccine encoding a chimeric protein of avian influenza hemagglutinin subtype H5 fused to CD154 (CD40L) in Pekin ducks," *Vaccine* 28(51), 8147-8156.

Yo, Y. T. et al. (2007) "Coexpression of Flt3 ligand and GM-CSF genes modulates immune responses induced by HER2//neu DNA vaccine," *Cancer Gene Therapy* 14(11), 904-917.

Young, N. J. et al. (2005) "Immune responses to non-structural protein 3 (NS3) of bovine viral diarrhoea virus (BVDV) in NS3 DNA vaccinated and naturally infected cattle," *Preventive Veterinary Medicine* 72(1-2), 115-120; discussion 215-119.

Zhu, J. et al. (2007) "Innate immune response to adenoviral vectors is mediated by both Toll-like receptor-dependent and -independent pathways," *Journal of Virology* 81(7), 3170-3180.

Zhuang, Y. et al. (2006) "Characterization of a phenotypically unique population of CD13+ dendritic cells resident in the spleen," *Clinical and Vaccine Immunology* 13(9), 1064-1069.

Zemmer, G. M. et al. (2002) "Failure of foetal protection after vaccination against an experimental infection with bovine virus diarrhea virus," *Veterinary Microbiology* 89(4), 255-265.

Zimmerman, A. D. et al. (2006) "Evaluation of protection against virulent bovine viral diarrhea virus type 2 in calves that had maternal antibodies and were vaccinated with a modified-live vaccine," *Journal of the American Veterinary Medical Association* 228(11), 1757-1761.

Zubkova, I. et al. (2009) "T-cell vaccines that elicit effective immune responses against HCV in chimpanzees may create greater immune pressure for viral mutation," *Vaccine* 27(19), 2594-2602.

PCT International Search Report of International Application No. PCT/US2013/059235 dated Dec. 13, 2013.

\* cited by examiner

| CD5 | V$_H$CC98 | A | V$_L$CC98 | B | N$^{pro}$ | Capsid | E$^{rns}$-E1 | E2 | FLAG |

Fig. 8B

| CD5 | V$_H$CC98 | A | V$_L$CC98 | B | NS2 | NS3 | FLAG |

FIG.9A

A) Tmpred output for CD5CC98-NcapE Chimera

FIG.9B

B) Tmpred output for CD5CC98-NS2-3 Chimera

| Group (n=5) | BVDV Vaccine | Adjuvant |
|---|---|---|
| A | AdCC98-NcapE$_{Singer}$ | AdFlt3L/AdGM-CSF/AdCD40L |
|  | AdCC98-NS2-3$_{Singer}$ |  |
|  | AdCC98-NcapE$_{296}$ |  |
|  | AdCC98-NS2-3$_{296}$ |  |
| B | AdIC-NcapE$_{Singer}$ | AdFlt3L/AdGM-CSF/AdCD40L |
|  | AdIC-NS2-3$_{Singer}$ |  |
|  | AdIC-NcapE$_{296}$ |  |
|  | AdIC-NS2-3$_{296}$ |  |
| C | AdCC98-NcapE$_{Singer}$ | Adluciferase |
|  | AdCC98-NS2-3$_{Singer}$ |  |
|  | AdCC98-NcapE$_{296}$ |  |
|  | AdCC98-NS2-3$_{296}$ |  |
| D | Adluciferase | AdFlt3L/AdGM-CSF/AdCD40L |

Figure 13

MOSAIC CHIMERIC VIRAL VACCINE PARTICLE

STATEMENT OF GOVERNMENT SUPPORT

This invention was made with government support awarded by the USDA-NIFA (USDA-CSREES 2008-35204-04587). The government has certain rights in the invention.

FIELD OF THE INVENTION

The present invention relates generally to the field of live and modified live conventional vaccines, and recombinant live-vectored vaccines. For example, compositions and methods axe described that are useful for priming robust adaptive immunity in the presence of pre-existing protective/neutralizing levels of maternal antibodies and/or effective boosting of weak immune responses using the same live vaccines or live-vectored vaccines. In some embodiments, simultaneously masking vaccines to avoid antibody neutralization while targeting those vaccines to specific cell types elicits an enhanced immune response. In other embodiments, the efficacy of the immune responses may be further enhanced using vectors that recruit and activate specific antigen-presenting cells.

BACKGROUND

Bovine viral diarrhea virus (BVDV) is a leading cause of enteric, respiratory and reproductive diseases in cattle, and is particularly associated with high morbidity and mortality rates in calves. There are more than 105 million cattle in the United States (USDA-NASS statistics, 2002) and the cattle industry accounts for approximately 40% of the total market value of U.S. agriculture (USDA, NASS statistics, 1999). Since endemic infections result in major economic loss, BVDV is considered a high priority disease of economic importance to U.S. animal agriculture.

While maternal antibodies protect neonatal calves and yearlings against wild-type (wt) BVDV infections, their high titers interfere with the efficacy of current BVDV vaccines. Thus, vaccination is normally delayed until the neutralizing maternal antibodies decay. Unfortunately, persistently infected (PI) calves are common in herds and yearlings become vulnerable to infection as BVDV-specific antibodies decline (12, 13, 15). Moreover, maternal antibodies do not adequately protect a significant proportion of neonatal calves—especially bull calves that fail to get sufficient amounts of colostrum on time.

What is needed is a vaccine capable of stimulating adaptive T cell immunity in neonatal calves in the presence of protective levels of colostrum-derived antibodies to facilitate the transition from transient passive immunity to acquired immunity without experiencing a period of vulnerability to BVDV infection.

SUMMARY OF THE INVENTION

In one embodiment, the present invention contemplates a bi-specific diabody comprising a virus-masking motif (or viral antigen binding moiety) fused in-frame with a cell-receptor binding motif (or cell surface antigen binding moiety). In one embodiment, the virus-masking motif (or viral antigen binding moiety) is a single chain antibody molecule that binds to BVDV. In another embodiment, the virus-masking motif (or viral antigen binding moiety) is a single chain antibody molecule that binds to the BVDV protein E2. In another embodiment, the cell-receptor binding motif (or cell surface antigen binding moiety) is a single chain antibody molecule that binds to dendritic cells. In yet another embodiment, the cell-receptor binding motif (or cell surface antigen binding moiety) is a single chain antibody molecule that binds to the bovine CD205 antigen receptor.

In one embodiment, the present invention contemplates a recombinant adenovirus that expresses dendritic cell recruitment and activation factors. In one embodiment, dendritic cell recruitment factors are cytokines. In another embodiment, the cytokines are Flt3L and GM-CSF. In another embodiment, the dendritic cell activation factor is CD40L. In yet another embodiment, the dendritic cell activation factor is an agonistic anti-CD40 monoclonal antibody.

In one embodiment, the present invention contemplates a viral vaccine particle coated with a bi-specific diabody comprising a viral antigen-specific masking motif (or viral antigen-specific binding moiety) fused in-frame with a dendritic cell receptor-specific binding motif (or cell surface antigen binding moiety). In one embodiment, the viral vaccine particle is a BVDV 1 modified live virus (MLV). In another embodiment, the viral vaccine particle is a BVDV 2 MLV. In another embodiment, viral vaccine particles are a mixture of BVDV 1 and BVDV 2 MLVs. In another embodiment, the viral vaccine particle is a target of neutralizing antibody. In another embodiment, the neutralizing antibody is maternal antibody. In one embodiment, the present invention contemplates a composition comprising a viral vaccine particle coated with a bi-specific diabody comprising a viral vaccine particle-masking motif (or viral vaccine particle antigen binding moiety) fused in-frame with a dendritic cell antigen receptor-specific binding motif (or cell surface antigen binding moiety), and a recombinant adenovirus that expresses dendritic cell recruitment and activation factors. In one embodiment, the dendritic cell recruitment factors are cytokines. In another embodiment, the cytokines are Flt3L and GM-CSF. In another embodiment, the dendritic cell activation factor is CD40L. In another embodiment, the dendritic cell activation factor is an agonistic anti-CD40 monoclonal antibody, diabody, or polyvalent diabody scaffold. In one embodiment, the viral vaccine particle is a BVDV 1 MLV. In another embodiment, the viral vaccine particle is a BVDV 2 MLV. In another embodiment, viral vaccine particle is a mixture of BVDV 1 and BVDV 2 MLV. In another embodiment, the viral vaccine particle is a target of neutralizing antibody. In another embodiment, the neutralizing antibody is maternal antibody. In one embodiment, the present invention contemplates a vaccine particle coated with a bi-specific diabody comprising a virus-masking motif (or viral antigen binding moiety) fused in-frame with a dendritic cell antigen receptor-specific binding motif (or cell surface antigen binding motif). In one embodiment, the vaccine is a BVDV 1 MLV. In another embodiment, the vaccine is a BVDV 2 MLV. In another embodiment, the vaccine is a mixture of BVDV 1 and BVDV 2 MLVs. In yet another embodiment, the vaccine is a live vaccine. In one embodiment, the live vaccine is a modified live vaccine. In one embodiment, the vaccine is a live vectored vaccine. In another embodiment, the vaccine evades neutralizing antibody. In another embodiment, the neutralizing antibody is maternal antibody. In yet another embodiment, the vaccine is targeted to dendritic cells. In one embodiment, the present invention contemplates a vaccine coated with a bi-specific diabody comprising a virus-masking motif (or viral antigen binding moiety) fused in-frame with an APC antigen receptor-specific binding motif (or cell surface antigen binding moiety), and a recombinant adenovirus that expresses dendritic cell recruitment and activation factors. In one embodiment, the dendritic cell recruitment factors are cytokines. In another embodiment, the cytokines are Flt3L and GM-CSF. In another embodiment, the activation factor is CD40L or agonistic anti-CD40 monoclonal antibody, diabody or polybody scaffold. In yet another embodiment, the vaccine is a BVDV 1 vaccine. In yet another embodiment, the vaccine is a BVDV 2 vaccine. In one embodiment, the vaccine is a mixture of BVDV 1 and BVDV 2 vaccines. In one embodiment, the vaccine is a live vaccine. In another embodiment, the live vaccine is a modified live vaccine. In another embodiment, the vaccine is a live vectored vaccine. In yet another embodiment, the vaccine evades neutralizing antibody. In yet another embodiment, the neutralizing antibody is maternal antibody. In one embodiment, the vaccine is targeted to dendritic cells. In one embodiment, the vaccine activates dendritic cells. In another embodiment, the vaccine recruits dendritic cells.

In one embodiment, the present invention contemplates a method, comprising providing a subject at risk for infection by a virus, and a viral vaccine particle coated with a bi-specific diabody comprising a viral vaccine particle-masking motif (or viral antigen binding moiety) fused in-frame with an APC antigen receptor-specific binding motif (or cell surface binding moiety) and administering the viral vaccine particle to the subject under conditions such that protective immunity is induced in said subject. In one embodiment, the viral vaccine particle is a BVDV 1 antigen. In another embodiment, the viral vaccine particle is a BVDV 2 antigen. In yet another embodiment, the viral vaccine particle is a mixture of BVDV 1 and BVDV 2 antigens. In one embodiment, the subject is a bovine. In another embodiment, the subject is a neonatal calf. In one embodiment, the subject has neutralizing antibodies for said viral vaccine particle prior to administering said viral vaccine particle. In another embodiment, the neutralizing antibodies are maternal antibodies. In another embodiment, the neutralizing antibodies are BVDV 1-specific antibodies. In yet another embodiment, the neutralizing antibodies are BVDV 2-specific antibodies. In yet another embodiment, the viral vaccine particle is a BVDV 1 vaccine. In one embodiment, the viral vaccine particle is a BVDV 2 vaccine. In yet another embodiment, the viral vaccine particle evades neutralizing antibody. In one embodiment, neutralizing antibody is maternal antibody. In one embodiment, the viral vaccine particle is targeted to dendritic cells.

In one embodiment, the present invention contemplates a method, comprising providing a subject at risk for infection by a virus, a viral vaccine particle coated with a bi-specific diabody comprising a viral vaccine particle-masking motif (or viral antigen binding moiety) fused in-frame with a dendritic cell antigen receptor-specific binding motif (or cell surface antigen binding moiety), and a recombinant adenovirus that expresses dendritic cell recruitment and activation factors and administering the viral antigen and recombinant adenovirus to the subject under conditions such that protective immunity is induced. In another embodiment, the subject is a bovine. In one embodiment, the viral vaccine particle is a BVDV 1 antigen. In another embodiment, the viral vaccine particle is a BVDV 2 antigen. In yet another embodiment, the viral vaccine particle is a mixture of BVDV 1 and BVDV 2 antigens. In yet another embodiment, the subject is a neonatal calf. In one embodiment, the dendritic cell recruitment factors are cytokines. In one embodiment, the cytokines are Flt3L and GM-CSF. In another embodiment, the activation factor is CD40L. In another embodiment, the activation factor is an agonistic anti-CD40 monoclonal antibody. In one embodiment, the viral vaccine particle evades neutralizing antibody. In another embodiment, the neutralizing antibody is maternal antibody. In yet another embodiment, the viral vaccine particle is targeted to dendritic cells.

In one embodiment, the present invention contemplates a method, comprising providing a subject at risk for infection by a virus, a vaccine coated with a bi-specific diabody comprising a virus vaccine particle-masking motif (or viral antigen binding moiety) fused in-frame with a dendritic cell antigen receptor-specific binding motif (or cell surface antigen binding moiety) and administering the vaccine to the subject under conditions such that protective immunity is induced. In another embodiment, the subject is a bovine. In yet another embodiment, the subject is a neonatal calf. In one embodiment, the subject has neutralizing antibodies for said virus vaccine particle prior to administering said vaccine. In another embodiment, the neutralizing antibodies are maternal antibodies. In another embodiment, the neutralizing antibodies are BVDV 1-specific antibodies. In yet another embodiment, the neutralizing antibodies are BVDV 2-specific antibodies. In yet another embodiment, the vaccine is a BVDV 1 vaccine. In one embodiment, the vaccine is a BVDV 2 vaccine. In one embodiment, the vaccine is a mixture of BVDV 1 and BVDV 2 vaccines. In another embodiment, the vaccine is a live vaccine. In another embodiment, the live vaccine is a modified live vaccine. In yet another embodiment, the vaccine is a live-vectored vaccine. In yet another embodiment, the vaccine evades neutralizing antibody. In one embodiment, neutralizing antibody is maternal antibody. In one embodiment, the vaccine binds to dendritic cells. In another embodiment, the vaccine activates dendritic cells. In yet another embodiment, the vaccine recruits dendritic cells.

In one embodiment, the present invention contemplates a method, comprising providing a subject at risk for infection by a virus, a vaccine coated with a bi-specific diabody comprising a virus vaccine particle-masking motif (or viral antigen binding moiety) fused in-frame with a dendritic cell antigen receptor-specific binding motif (or cell surface antigen binding moiety), and a recombinant adenovirus that expresses dendritic cell recruitment and activation factors and administering the vaccine and recombinant adenovirus to the subject under conditions such that protective immunity is induced. In another embodiment, the subject is a bovine. In yet another embodiment, the subject is a neonatal calf. In one embodiment, the dendritic cell recruitment factors are cytokines. In one embodiment, the cytokines are Flt3L and GM-CSF. In another embodiment, the activation factor is CD40L. In yet another embodiment, the activation factor is an agonistic anti-CD40 monoclonal antibody, or diabody, or polyvalent diabody scaffold. In one embodiment, the vaccine is a BVDV 1 vaccine. In another embodiment, the vaccine is a BVDV 2 vaccine. In yet another embodiment, the vaccine is a mixture of BVDV 1 and BVDV 2 vaccines. In yet another embodiment, the vaccine is a live vaccine. In one embodiment, the live vaccine is a modified live vaccine. In one embodiment, the vaccine is a live-vectored vaccine. In another embodiment, the vaccine evades neutralizing antibody. In another embodiment, the neutralizing antibody is maternal antibody. In yet another embodiment, the vaccine is targeted to dendritic cells. In yet another embodiment, the vaccine activates dendritic cells. In one embodiment, the vaccine recruits dendritic cells.

In one embodiment, the present invention contemplates a composition comprising a recombinant adenovirus that expresses multi-component chimeric BVDV mosaic antigens. In another embodiment, the chimeric mosaic antigens are selected from the group consisting of $N^{pro}$, capsid, $E^{ms}$-E1, E2, NS2, NS3. In one embodiment, the present invention contemplates the priming of protective immunity in neonatal calves by immunizing with a single dose of adenoviruses expressing Flt3L/GM-CSF/CD40L mixed with a DC-targeted MLV vaccine against BVDV 1 and 2. In another embodiment, the present invention contemplates the priming of protective BVDV-specific $CD4^+$ T helper and $CD8^+$ CTL responses. In yet another embodiment, the present invention contemplates the priming of protective BVDV-specific $CD4^+$ T helper and $CD8^+$ CTL responses in the presence of neutralizing antibodies. In one embodiment, the present invention contemplates priming protective immunity in neonatal calves by immunizing with a single dose of adenoviruses expressing Flt3L/GM-CSF/CD40L and DC-targeted BVDV antigens. In one embodiment, the present invention contemplates priming protective BVDV-specific $CD4^+$ T helper and $CD8^+$ CTL responses. In one embodiment, the present invention contemplates priming protective BVDV-specific $CD4^+$ T helper and $CD8^+$ CTL responses in the presence of neutralizing antibodies. In one embodiment, the present invention contemplates the immunization of neonatal calves with a single dose of a vaccine formulation containing adenoviruses expressing Flt3L/GM-CSF/CD40L (for DC recruitment and activation) and DC-targeted protective BVDV antigens. In one embodiment the vaccine formulation induces robust effector/memory $CD4^+$ and $CD8^+$ T cell responses that prime and expand cell-mediated immunity. In one embodiment, the vaccine formulation induces robust effector/memory $CD4^+$ and $CD8^+$ T cell responses that prime and expand cell-mediated immunity in the presence of neutralizing antibodies.

In one embodiment, the present invention contemplates improved BVDV vaccines that are efficacious in the presence of neutralizing antibodies. In another embodiment, the present invention contemplates inducing immunity in neonates that are not adequately protected by maternal antibodies. In another embodiment, the present invention contemplates vaccines capable of inducing robust adaptive T cell immunity against viruses, including but not limited to BVDV, in neonatal calves and yearlings.

In one embodiment, the present invention contemplates the production of recombinant diabodies in bacteria expression systems. In another embodiment, these diabodies may be used as additives in current commercially available MLV vaccines against BVDV 1 and 2.

In one embodiment, the present invention contemplates a method of determining whether a subject has been exposed to a naturally occurring antigen (including but not limited to viral antigens) or a recombinant antigen (including but not limited to recombinant viral antigens). In one embodiment, the recombinant antigen is a peptide or polypeptide comprising a FLAG-tag. In another embodiment, the recombinant antigen is expressed by a vaccine (i.e. a marker vaccine). In another embodiment, the recombinant antigen is expressed by an adenovirus vaccine. In another embodiment, the recombinant antigen is a BVDV1 peptide. In another embodiment, the recombinant antigen is a BVDV 2 peptide. In yet another embodiment, the recombinant antigen is an $N^{pro}$, capsid, $E^{ms}$-E1, E2, NS2 or NS3 peptide (or combinations thereof). In one embodiment, detecting exposure of a subject to recombinant antigen comprising a FLAG-tag identifies that subject as having been exposed to recombinant antigen. In another embodiment, detecting exposure of a subject to antigen that does not comprise a FLAG-tag identifies that subject as having been exposed to naturally occurring antigen.

While the present application focuses on BVDV to establish proof-of-concept, the approach is broadly applicable to live/modified live/live-vectored vaccines for both livestock and humans. It is not intended that the present invention be limited to BVDV. In one embodiment, the present invention contemplates bovine respiratory viruses, including but not limited to, bovine respiratory syncytial virus (BRSV), infectious bovine rhinotracheitis (IBR), bovine parainfluenza-3 virus (BPIV-3), bovine herpes virus 1 (BHV-1) and bovine herpes virus 2 (BHV-2). In another embodiment, the present invention contemplates bovine respiratory bacteria, including but not limited to, *pasteurella haemolytica, pasteurella multocida, haemophilus somnus* and *mycoplasma bovis*. In another embodiment, the present invention contemplates human virus, including but not limited to Measles, Rotavirus, Mumps, Rubella, and Varicella vaccines.

It is not intended that the present invention is limited to bovines. In one embodiment, the present invention contemplates inducing immunity in a variety of subjects, such as goats, sheep and humans.

DEFINITIONS

To facilitate the understanding of this invention a number of terms are defined below. Terms defined herein (unless otherwise specified) have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, terms defined in the singular are intended to include those terms defined in the plural and vice versa.

As used herein, the term "diabody" reference to a class of small bivalent and bi-specific antibody fragments that can be expressed with high yields. A diabody comprise a heavy ($V_H$) chain variable domain connected to a light chain variable domain ($V_L$) on the same polypeptide chain ($V_H$-$V_L$) connected by a peptide linker that is too short to allow pairing between the two domains on the same chain. This forces paring with the complementary domains of another chain and promotes the assembly of a dimeric molecule with two functional antigen binding sites. A bi-specific diabody may be constructed by fusing the V-domains of two separate antibodies (i.e. antibodies A and B) to create the two chains: $V_{HA}$-$V_{LB}$, $V_{HB}$-$V_{LA}$. Although each chain is inactive in binding to antigen, the functional antigen binding sites of antibodies A and B are recreated upon pairing with the other chain.

As used herein, the term "antibody" or "antibodies" refers to globular proteins ("immunoglobulins") produced by cells of the immune system to identify and neutralize foreign antigens. "Monoclonal antibodies" (mAb) are antibodies that recognize a specific antigenic epitope (i.e. monospecific) because they are derived from clones of a single hybridoma. Hybridomas are cells engineered to produce a desired mAb antibody in large amounts. Briefly, B-cells are removed from the spleen of an animal that has been challenged with the desired antigen. These B-cells are then fused with myeloma tumor cells that can grow indefinitely (i.e. immortal) in culture, Since the fused cell or hybridoma is also immortal it will multiply rapidly and indefinitely to produce large amounts of the desired mAb (Winter and Milstein, Nature, 349, 293-299, 1991). "Polyclonal antibodies" (pAb) are a mixture of antibodies that recognize multiple epitopes of a specific antigen. Polyclonal antibodies are produced by immunizing an animal (i.e. mouse, rabbit, goat, horse, sheep etc.) with a desired antigen to induce B-lymphocytes to produce antibodies to multiple epitopes of that antigen. These antibodies can then be isolated from the animal's blood using well-known methods, such as column chromatography.

As used herein, the term "dendritic cells" or "DCs" refers to immune cells that form part of the mammalian immune system. A primary function of DCs is to serve as "antigen-presenting cells" by processing foreign antigens and presenting antigenic epitopes on their surface to other cells of the immune system. DCs are present in small quantities in tissues that are in contact with the external environment, mainly the skin (where there is a specialized dendritic cell type called Langerhans cells) and the inner lining of the nose, lungs, stomach and intestines. DCs can also be found in an immature state in the blood. Once activated, they migrate to the lymphoid tissues where they interact with T cells and B cells to initiate the adaptive immune response. At certain development stages DCs grow branched projections (dendrites) that give the cell its name. In some embodiments, DCs can be differentiated into two sub-populations based on the expression of the cell surface marker CD11c. In some embodiments, CD11c$^+$ DCs produce IL12 and stimulate a Th1 response in lymphocytes, while CD11c$^-$ DCs synthesize little IL12 but are a major source of alpha-interferon and stimulate lymphocytes to produce Th2 cytokines.

As used herein, the term "cytokines" refers to a category of protein, peptide, or glycoprotein molecules secreted by specific cells of the immune system that carry signals between cells. Cytokines are a critical component of both the innate and adaptive immune response, and are often secreted by immune cells that have encountered a pathogen to activate and recruit additional immune cells to increase the system's response to the pathogen. Cytokines are typically released in the general region of the pathogen-infected cells such that responding immune cells arrive at that site of infection. Each individual cytokine has a matching cell-surface receptor. Upon binding of a cytokine to its cell-surface receptor a cascade of intracellular signaling events alters the cell's function. This includes the upregulation and/or downregulation of genes involved in the production of other cytokines, an increase expression of surface receptors for other molecules, or suppression of the cytokine itself by feedback inhibition. The effect of a particular cytokine on a given cell depends on the cytokine, its extracellular abundance, the presence and abundance of the complementary receptor on the cell surface, and downstream signals activated by receptor binding. Common cytokines include interleukins that are responsible for communication between white blood cells; chemokines that promote chemotaxis; and interferons that have anti-viral effects, such as shutting down protein synthesis in the host cell. Cytokines are characterized by considerable "redundancy", in that many cytokines appear to share similar functions. For example, "granulocyte-macrophage colony-stimulating factor" (GM-CSF) and "Fms-related tyrosine kinase 3 ligand" (Flt3L) are both cytokines that promote dendritic cell differentiation.

As used herein, the term "motif" or "peptide motif" refers to a conserved amino acid sequence. Naturally occurring proteins in cellular networks often share "peptide motifs" that play a pivotal role in protein interactions among the components of a network. Motifs are often associated with biological functions, protein structures or evolutionary history, and generally consist of short amino acids (typically 5-25 amino acids). Some peptide motifs lose their original biological functions when they are isolated from their parental proteins, indicating that peptide motifs are influenced by their context within the proteins.

As used herein, the term "cell-mediated immunity" refers to an immune response that does not involve antibodies or complement but rather involves the activation of macrophages, natural killer cells (NK), antigen-specific T-cells and the release of various cytokines in response to an antigen. Patterns of cytokine production by T cells are associated with different immunological responses, described as type-1 (Th-1) and type-2 (Th-2) responses. In some embodiments, the Th-1 response stimulates cell-mediated immunity by releasing cytokines such as IFN-γ, which increase the production of IL-12 by DCs and macrophages. In some embodiments, IL-12 also stimulates the production of IFN-γ by Th-1 cells by positive feedback.

As used herein, the term "chimera" when used in reference to a polypeptide refers to the expression product of two or more coding sequences obtained from different genes, that have been cloned together and that, after translation, act as a single polypeptide sequence. Chimeric polypeptides may also be referred to as "hybrid" polypeptides. The coding sequences include those obtained from the same or from different species of organisms. The protein can be engineered to include the full sequence of the original polypeptide, or a portion thereof. A chimera may serve various functions, including enhancement of solubility of the polypeptide of interest, antigen presentation for vaccines, to inhibit specific cellular pathways or process, or as an "affinity tag" to allow identification and/or purification of the chimera from a host cell or from a supernatant or from both. In-frame insertions of an exogenous gene or gene fragment into specific coding regions of the adenovirus genome, including for example genes encoding adenovirus capsid proteins, may result in the production of fusion proteins that are displayed on the capsid surface of biologically active adenovirus particles. Such "chimeric adenovirus" constructs may be used, for example, as vaccines to display specific antigens. Additionally, such constructs may combined as "hybrid vaccines" that simultaneously express and display antigenic peptide(s) along with proteins (including cytokines) that mediate DC recruitment and activation.

As used herein, the term "vaccine", "vaccinate" or "vaccination" refers to the introduction of a small amount of an antigen into an organism in order to trigger the immune system to generate activated B cells and/or sensitized T cells. These cells recognize and eliminate the foreign antigen and also establish immune system "memory" such that future exposures to the antigen result in its rapid recognition and clearance. A variety of antigenic substances may be used for vaccination, including live (i.e. non-attenuated), live-vectored, dead or inactivated (i.e. live attenuated or modified live) organisms (including viruses), or purified products derived therefrom. Vaccines can be used to prevent or ameliorate the effects of a future infection (i.e. prophylactic) or therapeutic, such as anti-cancer vaccine.

As used herein, the term "subject" refers to any mammal, preferably a human patient, livestock, companion animal or domestic pet.

As used herein, the term "FLAG-tag" or "FLAG-TAG" refers to a polypeptide (amino acid sequence N-DYKDDDDK-C (SEQ ID NO: 1)) that can be added to the C-terminal or N-terminal end of a protein for epitope tagging using recombinant DNA technology. FLAG-tags may be used in a number of epitope tagging applications, including for example, affinity chromatography to separate recombinant proteins from wild-type protein expressed by a host organism, isolation of protein complexes with multiple subunits and to distinguish between immunized (i.e. a FLAG-tagged vaccine or vaccine subunit) and naturally infected subjects. FLAG-tags may be used in a variety of assays that rely on recognition of the FLAG-tag by an antibody. For example, if an antibody specific for a protein of interest is not available, the addition of a FLAG-tag to that protein allows it to be detected with an antibody against the FLAG sequence (i.e. an anti-FLAG mAb), including for example an alkaline phosphatase (AP) labeled anti-FLAG mAb. FLAG-tags may be used in conjunction with other affinity tags, for example a polyhistidine tag (His-tag), hemagglutinin tag (HA-tag) or C-myc-tag.

As used herein, the term "fused", "fusion" or "fusion protein" when used in reference to a polypeptide refers to the joining of two or more genes which originally coded for separate proteins. The protein can be engineered to include the full sequence of the original proteins, or a portion thereof. Translation of this gene fusion results in a single polypeptide with functional properties derived from each of the original proteins. The fusion partner may serve various functions, including enhancement of solubility of the polypeptide of interest, antigen presentation for vaccines, to inhibit specific cellular pathways or process, or as an "affinity tag" to allow purification of the recombinant fusion polypeptide from a host cell or from a supernatant or from both. If desired, the fusion partner may be removed from the protein of interest after or during purification. In one embodiment, a "fusion protein" may be generated by removing the stop codon from a cDNA sequence coding for a first protein and then appending the cDNA sequence of the second protein "in frame" through ligation or overlap extension PCR such that the resulting DNA sequence will be expressed by a cell as a single protein. The "fusion protein" can be engineered to include the full sequence of both original proteins, or only a portion of either. In some embodiments, linker (or "spacer") peptides may be added between the first and second proteins so that the each protein folds independently to retain its original biological activity. In some embodiment, the linker peptides may enable protein purification. In other embodiments, the linker peptides contain cleavage sites for proteases or chemical agents that enable the liberation of each individual protein. This technique is often used for identification and purification of proteins, for example by fusing a GST protein, FLAG peptide or a hexa-his peptide (6×His-tag) which can be isolated using affinity chromatography with nickel or cobalt resins. Fusion proteins can also be manufactured with toxins or antibodies attached to them in order to study disease development.

As used herein, the term "mask", "masked", "masking" or grammatical equivalents thereof refers to the binding of an antigenic molecule (including for example, a viral vaccine, or antigenic subunit thereof) with a molecule (including for example a peptide or polypeptide) comprising at least one motif capable of binding (i.e. "coating") distinct "moieties" (i.e. antigenic determinants) present on the antigenic molecule such that it "escapes" or "evades" detection by cells of the immune system following introduction into a subject. It is not necessary that every antigenic determinant is bound or coated. In one embodiment there may be complete or partial coating of the antigenic determinants. In a preferred embodiment, at least 10%, at least 25%, at least 50%, at least 75%, or at least 90% of the antigenic determinants are bound. It is also not necessary that the antigenic molecule completely avoids detection by the immune system. In one embodiment the antigenic particle may completely or partially avoid detection by the immune system. In a preferred embodiment, at least 10%, at least 25%, at least 50%, at least 75%, or at least 90% of the antigenic molecules bound with a molecule avoid detection by the immune system.

BRIEF DESCRIPTION OF THE DRAWINGS

For a more complete understanding of the features and advantages of the present invention, reference is now made to the detailed description of the invention along with the accompanying figures.

FIG. 1 depicts Flt3L and GM-CSF recruitment of DCs to the intradermal immunization site. Cryostat section from a pre-inoculation biopsy probed with monoclonal antibody (mAb) TH97A (1A); section from a day 10 biopsy probed with mAb TH97A (1B); section from a day 10 biopsy probed with an isotype-matched negative control mAb (1C); and a day 10 biopsy section probed with secondary biotinylated goat anti-mouse mAb (1D).

FIG. 2 depicts the binding of bovine CD205-specific recombinant single chain antibody (rscFv) to skin DCs. Cryostat section probed with a mAb secreted by the hybridoma that was used to generate the rscFv (2A); cryostat section probed with the rscFv fused to an antigen (MSP1a) (2B); cryostat section probed with an isotype control scFv-MSP1 chimera (2C); and cryostat section probed with an isotype-matched control mAb (2D).

FIG. 3A-B depicts the immunization of calves with a single dose of a DNA vaccine. Immunization with a vaccine encoding a DC-targeted MSP1 antigen and expressing Flt3L/GM-CSF/CD40L primes a rapid T cell response (3A). Immunization with a vaccine capable of DC recruitment, CD205 antigen targeting and CD40L-directed DC activation primed and expanded a robust IFN-$\gamma^+$CD4$^+$ T cell response (3B).

FIG. 4 depicts a modified live virus (MLV) vaccine that is "masked" with a CD205-BVDV 1 & 2-specific antibody conjugate to protect against antibody-mediated lysis and target DCs.

FIG. 5 depicts recombinant adenoviruses (rAd) that express various cytokines. rAdFlt3L-infected cells are probed with soluble human Flt3-Fc receptor (5A); rAdGM-CSF-infected cells are probed with mAb GM-CSF 20.1 (5B); and 293 A cells infected with the rAdCD40L-infected cells are probed with anti-FLAG mAb (5C). Cells infected with a rAd-luciferase (Adluc) served as a negative control.

FIG. 6 depicts the binding of bovine CD205-specific recombinant scFv (CC98 scFv) to bovine CD205. pCD205 transfected 293-F cells probed with recombinant CC98 scFv (6A); pCD205 transfected 293-F cells probed with the negative control recombinant IC scFv (6B); pCD205 transfected 293-F cells probed with the mouse anti-bovine CD205 mAb CC98 (6C); pCD205 transfected 293-F cells probed with an isotype-matched control mAb (6D); and pCD205 transfected 293-F cells probed with recombinant CC98MSP1a protein (6E).

FIG. 7 depicts the structure of the CC98-348 single chain diabody. The N-terminal CD5 secretory signal sequence, arrangement of the variable domains as well as the linker sequences A ($G_4S$) (SEQ ID NO: 2) and B ($G_4SG_2RASG_4SG_4S$) (SEQ ID NO: 3), and the C-terminal FLAG tag are shown.

FIG. 8A-B depicts the structure of adenoviruses expressing chimeric BVDV antigens. The structure of the CC98-

NcapE chimera (FIG. 8A) consists of the CD5 secretory signal sequence, the CC98 variable domains, linker sequences A (G$_4$S)$_3$ (SEQ ID NO: 4) and B (C$_4$S) (SEQ ID NO: 5), hydrophilic domains of NP$^{pro}$, capsid, E$^{rns}$, E1-E2, and the FLAG tag. The structure of the CC98-NS2-3 chimera (FIG. 8B) consists of the CD5 secretory signal sequence, the CC98 variable domains, linker sequences A (G$_4$S)$_3$ (SEQ ID NO: 4) and B (G$_4$S) (SEQ ID NO: 5), hydrophilic domains of NS2, NS3 and the FLAG tag.

FIG. 9A-B depicts the hydropathic profiles of the BVDV chimeric proteins CD5CC98-NcapE (9A); and CD5CC98-NS2-3 (9B).

Figure 12:
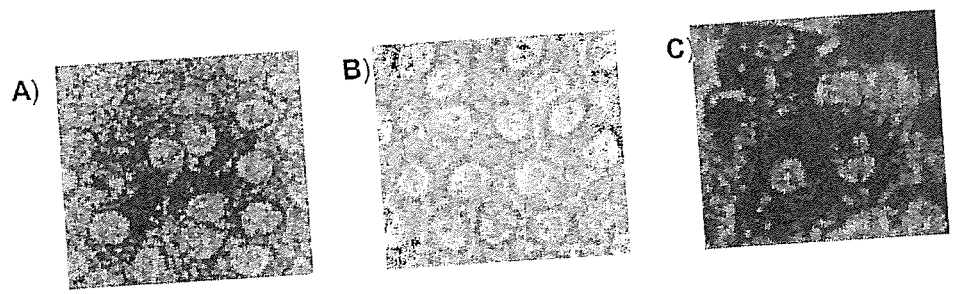

FIG. 12 depicts an immunocytochemistry evaluation of BVDV targeting to CD205 by the CC98-348 conjugate. CC98-348 conjugate was pre-incubated with BVDV and layered on CD205 transfected 293A cells. The CC98-348 conjugate plus virus was eluted with low pH buffer and transferred to MDBK cells (12A). Negative control was similarly treated but with unconjugated mAbs CC98 plus 348 (12B); Positive control was BVD virus that was subjected to the same pH treatment (12C).

FIG. 13 depicts the strategy for inoculating calves with BVDV vaccines mixed with adjuvant. Calves are inoculated intradermally with a single dose of a rAd expressing DC-targeted BVDV antigens mixed with either the rAd expressing cytokines (A) or the Adluciferase control (C). Calves are also inoculated with a mixture of the rAd expressing non-targeted BVDV antigens mixed with the rAd expressing cytokines (B), whereas other calves are inoculated with the Adluciferase control mixed with the rAd expressing cytokines (D).

DETAILED DESCRIPTION OF THE INVENTION

The present invention relates generally to the field of live and modified live, conventional and recombinant, vaccines. For example, compositions and methods are described that are useful for priming protective immunity in the presence of pre-existing maternal antibody. In some embodiments, simultaneously masking vaccines to avoid antibody neutralization while targeting those vaccines to specific cell types elicits an enhanced immune response. In other embodiments, the efficacy of the immune responses may be further enhanced using vectors that recruit and activate specific antigen-presenting cells.

I. Bovine Viral Diarrhea Virus

Bovine Viral Diarrhea Virus (BVDV) is a leading cause of enteric, respiratory, and reproductive diseases in cattle, which results in significant economic losses in the cattle industry (1). BVDV is a small, enveloped, single-stranded RNA virus that is a member of the genus *Pestivirus* in the family Flaviviridae. Other closely related pestiviruses include Classical Mille fever virus (CSFV) and ovine Border disease virus (BDV). The approximately 12.5 kb BVDV genome is flanked by 5' and 3' non-coding regions and consists of a single open reading frame (ORF) that encodes a 450 kDa precursor polyprotein that is processed by host and viral proteases to produce several structural and non-structural proteins (2, 3). The N$^{pro}$, capsid protein, and glycoproteins E$^{rns}$, E1, and E2, constitute the structural components of the virion, whereas NS2-3, NS4A-B, and NS5A-B constitute non-structural proteins (4-6). Resolution of acute BVDV infection requires cell-mediated immunity and significant portions of the N$^{pro}$, capsid, E$^{rns}$, E2, and NS2-3 antigens are highly conserved among BVDV strains and represent ideal targets for protection against multiple BVDV strains (32). The N$^{pro}$, capsid, E$^{rns}$, E2, and NS2-3 antigens contain B and T cell determinants that confer protection against infection with wt virus (20, 22, 23, 26-28). While several BVDV sub-unit vaccines based on these antigens have shown promising results, none of them have been used to date (41, 42, 83-85). BVDV is classified into genotypes 1 and 2 based on antigenic differences, as well as cytopathic (CP) and non-cytopathic (NCP) biotypes based on the presence or absence of cytopathic effect (CPE) in infected cell cultures (7-9). Classical BVDV infections cause severe diarrhea and respiratory disease, which is the most common cause of morbidity and mortality in feedyards (1). BVDV infections may also cause immunosuppression, abortion, stillbirth, congenital malformations, and the birth of persistently infected (PI) calves—the primary source of BVDV in cattle herds (7, 10, 11). A significant proportion of cattle entering feedyards are PI, and since a chute side test to identify these individuals is currently unavailable these calves pose a great risk to unprotected cattle (12, 13).

a) BVDV Immunity and Vaccines

The initial control of BVDV infection in neonates and yearlings is conferred by colostrum-derived BVDV-specific neutralizing antibodies (14). The rate of neutralizing antibody decay in neonates correlates to antibody titer at the early age and is influenced by many factors. Consequently, a high risk of infection exists, especially in the presence of PI calves in the herd, when calves become vulnerable to BVDV as their neutralizing antibodies wane (14-16). While neutralizing antibodies provide protection against wt BVDV infection, CD4$^+$ T cells are critical for clearance of infected cells (20, 21) due to their requirement in generating high affinity neutralizing antibody as well as optimal expansion and maintenance of CD8$^+$ cytotoxic T cells (22). In addition to these "helper" roles, CD4$^+$ T cells (as well as CD8$^+$ T cells) can be directly cytotoxic towards BVDV infected cells. BVDV-specific CD4$^+$ and CD8$^+$ T cells have been shown to be present within protected animals (22, 23). Consequently, one embodiment of the present invention contemplates the development of vaccines capable of priming and expanding protective BVDV-specific effector/memory CD4$^+$ and CD8$^+$ T cell responses in neonates. Still further embodiments contemplate improved priming and expanding of protective BVDV-specific effector/memory CD4$^+$ and CD8$^+$ T cell responses in the presence of neutralizing antibody for uniform control of BVDV infection in calves and yearlings.

Modified live BVDV and killed whole BVDV represent the primary vaccines available in the market. MLV vaccines are more efficacious than killed vaccines partly because the live virus infects vaccinates and replicates in vivo and thus delivers a more persistent antigen stimulus for B and T cell priming. Importantly, the virus generates high copies of its single-stranded RNA and the double-stranded intermediates which are ligands for TLR 7/8 and 3, respectively, and thus induce TLR-dependent pro-inflammatory responses that influence immune responses (73, 102, 103). MLV vaccines against BVDV also confer cross-protective immunity against different strains by inducing BVDV-specific neutralizing antibody, CD4+ and CD8+ T cells (18). Despite their ability to induce long lasting neutralizing antibodies and cell-mediated immunity, MLV vaccines have been known to cause mucosal disease, immunosuppression and in utero infections. Furthermore, MLV vaccines carry the risk of vaccine contamination with adventitious viruses and are ineffective in the presence of neutralizing antibodies (17, 82, 105).

In contrast, killed (or inactivated) vaccines stimulate antibody responses that induce short-lived immunity, fail to induce cross-reactive immunity to different BVDV strains (19) and generate weak T-cell mediated responses that do not stimulate cytolytic T cells (106). Inactivated vaccines do not provide protection to fetal infections and tend to loose immunogenicity during preparation (107-109). Consequently, there is a need to generate alternative BVDV vaccines that are efficacious, safe, cost-effective, and non-susceptible to BVDV-specific antibody neutralization.

i) Antibody-dependent BVDV Vaccine Inactivation

MLV vaccines against BVDV prime protective antibody and T cell immunity but their efficacy is limited until neutralizing antibody levels have waned. MLV vaccines are more efficacious than killed BVDV vaccines partly because the live virus infects, vaccinates and replicates in vivo and thus delivers a more persistent antigen stimulus for B and T cell priming. However, in the presence of BVDV-specific neutralizing antibodies, as is the case in neonates with maternal antibodies, the antibody binds to the vaccine virus and antibody-mediated complement lysis and opsonization rapidly clears the virus, thus impairing effective priming (24, 25). In one embodiment, the present invention contemplates masking a MLV BVDV vaccine to protect it against complement lysis and thus allow targeting of the virus to the relevant antigen-presenting cells (APCs) for optimal induction of adaptive immunity.

ii) Protective BVDV Antigens

The E2 and NS2-3 BVDV antigens are immunodominant, and neutralizing antibody as well as T cell responses directed against these antigens can confer protection against infection with wt virus (20, 22, 23, 26-28). The E2 envelope protein plays a major role in virus attachment and entry. Virus neutralization activity has been demonstrated predominantly for E2-specific antibodies, whereas the NS3 protein functions as a serine protease and RNA helicase; several B and T cell epitopes recognized by immune cattle have been identified (17, 26, 27, 29, 30). Cell-mediated immunity is required to resolve BVDV-infected cells and in vivo depletion of CD4+ T cells delays resolution of acute infection (20, 21). Importantly, evaluation of BVDV-specific immune responses following resolution of acute infection has revealed that the E2, NS2-3, capsid and $N^{pro}$ antigens are CD4+ T-cell determinants (23). In addition, major histocompatibility complex (MHC) DR-restricted T cell epitopes have been identified from conserved regions of E2 and NS2-3, and a large pool of potential MHC class I allele-specific cytotoxic T cell peptide motifs from the BVDV polyprotein have been predicted (28, 31). Significant portions of the E2, NS2-3, $N^{pro}$ and capsid antigens are highly conserved among BVDV strains and represent potential targets for the development of T cell vaccines for protection against multiple BVD virus strains (32). In one embodiment, the present invention contemplates a vectored live vaccine expressing chimeric genes encoding protective BVDV antigens optimized for induction of robust effector/memory CD4+ and CD8+ T cell responses that will induce cell-mediated immunity in neonatal calves in the presence of neutralizing maternal antibodies.

Dendritic Cells

Dendritic cells (DCs) have the unique ability to prime naïve T cells to become effector/memory T cells. Furthermore, DC antigen uptake can be influenced to enhance initiation of adaptive immunity. Flt3L and GM-CSF are molecular adjuvants (i.e. cytokines) that have been shown to enhance DC recruitment and vaccine efficacy in cattle, humans, and mice (69, 92, 93). Previous results have demonstrated that Flt3L and GM-CSF increase DC recruitment and significantly enhances antigen-specific CD4+ T cell responses and IFN-γ secretion in calves with diverse MHC class II haplotypes. A motif has been developed for directing high-affinity DC-vaccine interaction to enhance DC antigen uptake for optimal T cell priming. In addition, immunization of calves with a single dose of a DNA vaccine capable of DC recruitment, DC antigen targeting and DC activation, has been demonstrated to prime robust IFN-γ+CD4+ T cell responses that undergo rapid recall upon boost. To improve priming of BVDV-specific adaptive immunity in neonates, one embodiment contemplates expanding previous achievements in DC recruitment, antigen targeting and activation to develop and evaluate the efficacy of the following contemporary BVDV vaccines: 1) A DC-targeted MLV BVDV vaccine capable of evading antibody neutralization; and 2) recombinant adenoviruses expressing protective BVDV antigen chimeras optimized for induction of robust CD4+ and CD8+ T cell responses. A central hypothesis to be examined with these BVDV vaccines is that immunization of neonatal calves with a single dose of a formulation containing adenoviruses expressing DC recruitment and activation factors, and a DC-targeted MLV BVDV vaccine capable of evading neutralizing antibodies or adenoviruses expressing DC-targeted chimeric BVDV antigens will prime and expand protective effector/memory CD4+ and CD8+ T cells.

Langerhan cell (LC)-derived DCs preferentially activate cellular immunity and express high levels of CD205, which is involved in receptor-mediated antigen uptake through endocytosis (62-64). In one embodiment, priming of T cell immunity may be enhanced by targeting antigen to LCs. Importantly, antigens taken up by CD205 are presented by class I and class II molecules, with CD205-targeted antigen presented at least 400 times more efficiently than free antigen (66). Surprisingly, targeting an antigen to CD205 using anti-CD205 antibody enhances systemic as well as mucosal antigen-specific CD4+ and CD8+ T cell responses by greater than 1000 fold in a mouse model (67).

III. Adenoviruses a) Adenovirus Antigen Delivery System

Replication-defective adenovirus vectors are attractive vaccine vehicles since they direct high transgene expression, are species-specific, and induce both innate and adaptive immune responses in mammalian hosts, in part, by DC modulation through Toll-Like Receptor (TLR)-dependent and -independent pathways (33-35). A single dose immunization with an adenovirus-vectored vaccine induces stronger cytotoxic T-cell responses than recombinant vaccinia virus vector, plasmid DNA, or a combination of the two (36). Importantly, adenovirus-vectored vaccines can be administered via multiple routes such as intradermal and intranasal for induction of systemic and mucosal immunity (37-39). In addition, adenovirus transduces LCs efficiently and immunization of neonates at birth with a single dose of an adenovirus-vectored vaccine induces robust immune responses (38, 40). Current adenovirus vectors are safe, can accommodate and express large transgenes, replicate at high titers in complementing cell lines, and their production is scalable and reproducible (34). Adenovirus vectors have been used to express BVDV antigens and to induce protective immunity in cattle (39, 41, 42). Replication-defective human adenovirus vectors are capable of inducing protective immunity in neonatal calves in the presence of high neutralizing antibodies, and a single dose of an adenovirus-vectored vaccine induces robust immune responses in neonates (33-35, 39, 41, 42). Furthermore, adenoviruses have been used to express cytokines for DC recruitment and activation (43, 44). In one embodiment, the present invention contemplates the use of adenoviruses expressing chimeras containing protective BVDV antigens optimized for induction of robust $CD4^+$ and $CD8^+$ T cell responses to induce cell-mediated immunity in neonatal calves in the presence of neutralizing maternal antibodies.

IV. Antigen Processing a) Antigen Processing and Presentation

Antigen processing and presentation are key events for induction, expansion and maintenance of antigen-specific T cells. DCs are rare but highly specialized professional APCs that have a unique ability to prime naïve T cells to become protective antigen-specific effector as well as memory T cells (45, 46). The mechanism of antigen uptake by DCs determines the type of T cell epitopes generated (47). Antigens from pathogens, such as BVDV (48), that infect DCs and access the cytoplasm are processed by the proteosome and are presented to $CD8^+$ T cells by MHC class I molecules, whereas exogenous antigens are processed in the endosome/lysosome compartments and are presented to $CD4^+$ T cells by MHC class II molecules (49, 50). DCs can also cross-present antigens from these processing pathways as well as antigens released from other cells (51, 52).

In one embodiment, presentation of epitopes to T cells by DCs occurs in three distinct steps. First, maturing DCs in peripheral tissues function as sentinels, capturing antigen using specific receptors, phagocytosis or by uptake in the fluid phase, and then migrate to the draining lymphoid organs (45, 46). Antigen acquisition is followed by antigen processing and formation of peptide-MHC complexes. In the presence of sustained antigen uptake as well as supply of MHC molecules, these complexes progressively accumulate on DC surfaces (53, 54). The third step is T cell recognition whereby as few as 100 peptide-MHC complexes serially engage and trigger as many as 18,000 T cell receptors (55-57). Primed T cells then undergo clonal expansion to become circulating effectors, which are short-lived or memory cells ready to respond to recall antigen (58). In one embodiment, the present invention contemplates targeting a masked MLV BVDV vaccine or adenovirus-expressed protective BVDV antigen chimera to DCs in neonates to enhance priming of BVDV-specific T cells that will in turn provide quality help to B cells for optimal antibody responses and improved vaccine efficacy.

V. Targeting and Masking a) Targeting High-Affinity DC-BVDV Antigen Interaction to Enhance Priming DCs are the key APCs required for optimal induction of a primary immune response following vaccination—not macrophages or B cells. However, the frequency of DCs in tissues is less than 1% of all nucleated cells (59-61). Consequently, a vaccine that contains factors for DC recruitment and a motif that directs efficient targeting of a "masked" MLV BVDV vaccine or adenovirus-expressed BVDV antigens to a DC antigen receptor with high affinity may significantly increase the amount of antigen taken up by DCs as well as the number of DCs processing and presenting BVDV antigens, thus enhancing priming of BVDV-specific T cells in neonates with neutralizing antibodies.

Figure 1:
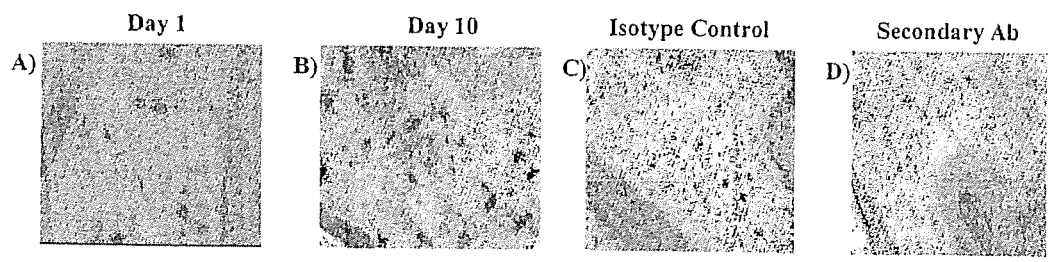
Figure 2:
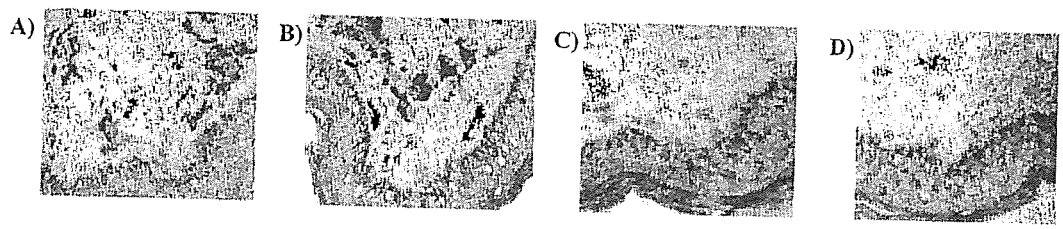

Maturing LC-derived DCs in the skin express high levels of CD205, which is involved in receptor-mediated antigen uptake through endocytosis (62). LC-derived DCs are confined to the T cell-rich zone in the draining lymph nodes where they preferentially activate cellular immunity, whereas dermal DCs are located just beneath the B cell follicles and appear to preferentially activate humoral immunity (63-65) and thus, antigen targeting to LCs should enhance priming of effector/memory T cell immunity. Importantly, antigens taken up by CD205 are processed and presented by MHC class I and class II molecules, and a CD205-targeted antigen is presented at least 400 times more efficiently than free antigen (66). Surprisingly, targeting an antigen to CD205 using anti-CD205 antibody enhances systemic as well as mucosal antigen-specific $CD4^+$ and $CD8^+$ T cell responses by >1000 fold in a mouse model (67). Furthermore, targeting an antigen to maturing, but not mature, DCs renders non-immunogenic antigens immunogenic and induces significant protective cellular immunity in a mouse model (68). Previous results demonstrate that Flt3L and GM-CSF increases DC recruitment to the intradermal immunization site (FIG. 1) and significantly enhances antigen-specific $CD4^+$ T cell responses and IFN-γ secretion in calves with diverse MHC class II haplotypes (69). A minimal single-chain antibody (scFv)-based motif for directing high-affinity DC-vaccine interaction to enhance DC antigen uptake for optimal T cell priming has also been developed (FIG. 2). Furthermore, results demonstrate that immunization of calves with a single dose of a DNA vaccine capable of DC recruitment, CD205 antigen targeting and CD40L-directed DC activation, prime and expand robust IFN-γ$^+$ $CD4^+$ T cell responses (FIGS. 3A-B) that undergo rapid recall upon boost (70). In one embodiment of the present invention, protective $CD4^+$ and $CD8^+$ T cell immunity is induced in the presence of BVDV neutralizing antibodies following the immunization of neonatal calves with a single dose of a formulation containing 1) adenoviruses expressing DC recruitment (Flt3L/GM-CSF) and activation (CD40L) factors, and either 2) a DC-targeted MLV BVDV vaccine capable of evading neutralizing antibodies or 3) adenovirus expressing DC-targeted chimeric BVDV antigens.

b) Activation of BVDV Antigen-Loaded DCs to Enhance Priming

Naïve T cells require two distinct signals from APCs for proper activation and induction of differentiation: the first signal is provided by peptide antigens in the context of MHC molecules, the second signal is delivered by co-stimulatory molecules such as CD80 or CD86 present on DCs (71). For antigen-loaded DCs to provide these signals effectively, they require activation to up-regulate surface expression of MHC-peptide complexes and co-stimulatory molecules, and to secrete pro-inflammatory molecules such as IL-12 (72). DC activation is an innate response that adjuvants as well as live vaccines stimulate through TLR signaling, chemokine and cytokine secretion (73). Expression of CD80/CD86 is upregulated by TLR ligands, TNF-α and IFN-γ as well as interaction between CD40 on DCs and CD40 ligand (CD40L) expressed by activated T lymphocytes (71-73). However, DCs from $CD40^{-/-}$ and $CD40^{-/-}L$ mice do not elicit $CD4^+$ and $CD8^+$ T cell immunity, even though the DCs present antigen on MHC class I and II molecules and express high levels of CD80/86 (72). A distinct CD40/CD40L signal that functions together with antigen presentation and co-stimulation is required to generate functional $CD4^+$ T helper and $CD8^+$ CTLs (72). This signaling critically requires APC-T cell contact, local CD40L secretion, or an agonistic anti-CD40 antibody (67, 74, 75). Furthermore, this signaling results in increased production of pro-inflammatory cytokines such as IL-12, which is a powerful inducer of IFN-γ production and Th1 differentiation (76). More importantly, DC activation through CD40 signaling overcomes tolerance and may release immature DCs from the control of regulatory $CD4^+CD25^+$ T cells (77). In one embodiment of the present invention, immunization of neonatal calves with a single dose of a formulation containing adenoviruses expressing Flt3L/GM-CSF for DC recruitment, CD40L for DC activation, mixed with a DC-targeted MLV BVDV vaccine capable of evading neutralizing antibodies or adenoviruses expressing DC-targeted chimeric BVDV antigens induces protective $CD4^+$ and $CD8^+$ T cell immunity in the presence of neutralizing antibodies.

c) In vivo Enhancement BVDV-Specific T Cell Immunity in Neonates

Heightened and improved protection of neonatal calves and yearlings against BVDV infection requires effective generation and preservation of BVDV-specific immunological memory. The potential of a vaccine formulation containing adenoviruses expressing Flt3L/GM-CSF/CD40L mixed with a DC-targeted "masked" MLV BVDV vaccine or adenoviruses expressing DC-targeted chimeric BVDV antigens to enhance priming and expansion of protective BVDV-specific $CD4^+$ and $CD8^+$ T cell responses is evaluated in neonatal calves with protective titers of BVDV neutralizing antibodies, More importantly, the efficacy of such BVDV vaccine formulations to confer protection is evaluated upon challenge following decline of passive immunity.

Figure 4:
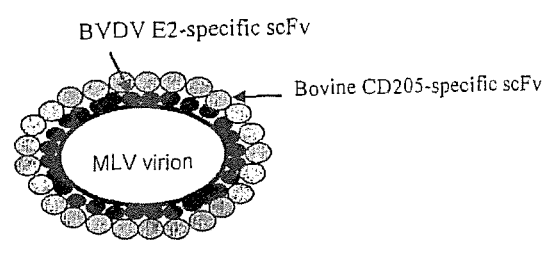

Immunization of young seronegative calves with a single dose of a MLV vaccine against BVDV confers protection and thus neonates are immune competent (78). A MLV vaccine is very susceptible to neutralization by antibodies but the vaccine can be masked to create a coat around the virion; that coat may be modified to contain a motif(s) for targeting the vaccine to DCs. As depicted in FIG. 4, the CD205-BVDV E2-specific diabody (CD205-E2) coats MLV vaccine virions to protect them from antibody-mediated complement lysis and target the coated virions to DCs. For example, in one embodiment the present invention contemplates a diabody consisting of the bovine CD205-specific mAb scFv for DC-antigen targeting (designated CC98) fused in-frame to a BVDV E2 antigen-specific scFv generated from a mAb specific for an epitope of BVDV 1 and 2 (79). Addition of the CC98-348 diabody to a commercially available MLV vaccine against BVDV 1 and 2 will generate a DC-targeted "masked" vaccine. This strategy has been used to target recombinant adenoviruses to specific cell types (80, 81). In one embodiment the present invention contemplates that intradermal inoculation of neonatal calves with a single dose of a vaccine formulation containing adenoviruses expressing Flt3L/GM-CSF/CD40L mixed with CC98-348-coated MLV vaccine against BVDV 1 and 2 will prime and expand protective BVDV-specific $CD4^+$ and $CD8^+$ T cell responses.

Although MLV vaccines against BVDV are efficacious in adults, they are known to cause mucosal disease, immunosuppression, in utero infection and carry the risk of vaccine contamination with adventitious viruses (17, 82). In an attempt to develop improved vaccines, several recombinant protein, DNA, and live-vectored BVDV sub-unit vaccines have been generated using the genes encoding the E2, NS2-3, capsid, and $N_{PRO}$ antigens; however there is no commercially available subunit vaccine against BVDV (41, 42, 83-85). Recombinant DNA and live-vectored BVDV subunit vaccines can overcome neutralizing maternal antibodies and induce T cell immunity in neonatal calves. However, a recombinant live vaccine with a comprehensive representation of protective B and T cell determinants from BVDV 1 and 2 has yet to be developed and tested in neonatal calves. In one embodiment, the present invention contemplates developing a contemporary vaccine against BVDV using a chimeric gene generated by fusing the DNA sequences encoding hydrophilic domains of consensus amino acid sequences generated by aligning the $N^{pro}$, capsid, $E^{ms}$, E1, and E2 polypeptide sequences of sequenced BVDV 1 and 2 genomes. This alignment generates a mosaic chimera that captures the antigen repertoire of currently known BVDV isolates. In a preferred embodiment of the present invention, immunization with the mosaic chimeric antigen confers broad protection against BVDV 1 and 2. In a preferred embodiment, this chimera may be modified to contain the sequences encoding the CC98 DC-targeting motif (FIG. 2) at the 5' end and the flag-tag sequence at the 3' end (69, 86), and the resulting chimeric gene is used to generate a recombinant adenovirus. Similarly, in one embodiment the sequences encoding the hydrophilic domains of the NS2-3 antigens may be used to generate a recombinant adenovirus expressing a DC-targeted NS2-3 mosaic chimera. Control adenoviruses may be similarly generated using an isotype-matched control scFv (designated IC) (FIG. 2). In one embodiment, immunization of calves with a single dose of a vaccine formulation containing adenoviruses expressing Flt3L/GM-CSF for DC recruitment, CD40-L for DC activation, and DC-targeted protective BVDV antigens optimized for induction of robust effector/memory $CD4^+$ and $CD8^+$ T cell responses will induce cell-mediated immunity in neonatal calves in the presence of neutralizing antibodies.

In one embodiment, the present invention contemplates inducing broad cell-mediated immunity in neonatal calves in the presence of neutralizing maternal antibodies by immunizing neonatal calves with a single dose of a vaccine formulation containing adenoviruses expressing Flt3L/GM-CSF/CD40L mixed with 1) a DC-targeted MLV BVDV vaccine capable of evading neutralizing antibodies, or 2) an adenoviruses expressing DC-targeted mosaic BVDV antigens optimized for induction of robust effector/memory $CD4^+$ and $CD8^+$ T cell responses.

Experimental

The following are examples that further illustrate embodiments contemplated by the present invention. It is not intended that these examples provide any limitations on the present invention. In the experimental disclosure that follows, the following abbreviations apply: eq. or eqs. (equivalents); M (Molar); μM (micromolar); N (Normal); mol (moles); mmol (millimoles); μmol (micromoles); nmol (nanomoles); pmoles (picomoles); g (grams); mg (milligrams); μg (micrograms); rig (nanogram); vol (volume); w/v (weight to volume); v/v (volume to volume); L (liters); ml (milliliters);. μl (microliters); cm (centimeters); mm (millimeters); μm (micrometers); nm (nanometers); C (degrees Centigrade); rpm (revolutions per minute); DNA (deoxyribonucleic acid); kDa (kilodaltons); kb (kilobase).

Effective control and long-term containment of BVDV requires the development of vaccines capable of stimulating robust effector/memory B and T cell immunity in neonatal calves and yearlings. An optimal vaccine should induce immunity in neonates that are not adequately protected by colostrum-derived antibodies thereby avoiding the period of vulnerability to infection as passive immunity wanes.

Results described herein extend the present inventors previous achievements in bovine DC recruitment, antigen targeting and activation to develop contemporary BVDV vaccines for effective priming of BVDV-specific adaptive immunity in neonates in the presence of neutralizing antibodies. In one embodiment, the vaccine optimization strategies disclosed herein augment BVDV vaccine immunogenicity at a single DC level. In a preferred embodiment, BVDV vaccine immunogenicity is augmented by employing: 1) Flt3L/GM-CSF to attract DCs to the immunization site, 2) CD40L (and the adenovirus vector itself) to provide potent TLR-dependent and -independent DC activation, and 3) the CC98-348 diabody to protect and target the MLV vaccine against BVDV 1 and 2 to DCs; wherein the CC98 scFv motif provides the specificity required for DC antigen targeting of protective BVDV antigens.

I. Bi-Specific Diabody Production a) Monoclonal Antibody Production

Monoclonal antibody (mAb) production involves a series of steps known to those skilled in the art, including (for example) antigen isolation, lymphocyte stimulation, myeloma cell fusion, identification of mAb-secreting cells and characterization of mAb specificity and affinity. Briefly, antibody producing lymphocytes are stimulated by in vitro or in vivo by immunization of an animal with a preparation of a desired antigen, including for example, BVDV 1 and 2 antigens such as $N^{pro}$, capsid, $E^{ms}$-E1, E2, NS2 and NS3. Spleens are removed from the immunized animals 72 hours following the last antigen boost and placed in Dulbecco's minimal essential medium (DMEM) supplemented with 4.5 gm/L of glucose 1000 U/ml of penicillin and 100 82 g/ml streptomycin. The spleens are teased apart with 25 gauge needles and the splenocytes are washed three times with DMEM prior to being resuspended at a constant concentration in DMEM. In general approximately 100 million cells are obtained from each spleen. The splenocyte suspension is then mixed with a continuously proliferating myeloma cell line in 96 well microtiter plates to generate cell fusions. The myeloma cells are sensitive to hypoxanthine-aminopterin-thymidine (HAT) medium by virtue of their lacking enzymes such as thymidine kinase (TK) or hypoxanthine-guanine phosphoribosyl transferase (HGPRT). This allows selection of hybrids to be accomplished by growth in HAT medium. Myeloma cell lines utilized for cell fusions may be derived from a BALB/c mouse MOPC 21 myeloma as described by Kholer et al, Eur. 3. Immunol., Vol. 6, pp. 292-295 (1976). Fused cells are grown in DMEM supplemented with 4.5 gm/l glucose, 20 mm glutamine, 1000 U/ml penicillin, 100 μg/ml streptomycin and 20% fetal calf serum (complete medium).

Microtiter wells are screened for cell proliferation 10 to 20 days following cell fusion. The mAbs secreted by individual clones are assayed for their ability to bind to the target antigen using assays such as ELISA, antigen microarray assay or immuno-dot blot. Hybridoma cells identified as positive secretors of the desired mAb are serially passaged to establish continuously proliferating cell lines with relatively stable genetic constitutions. These cell lines or clones are propagated indefinitely in tissue culture or in viva in syngeneic or immunocompromised hosts where they continue to synthesize and secrete antibody to the hepatitis viral antigens. The remaining cells are frozen and stored under liquid nitrogen.

Three separate assays may be used to screen mAbs secreted from individual clones for BVDV antigen specificity and affinity. In the first phase, one hundred and twenty μl of culture supernatant is removed from the microtiter plates and diluted to 200 μl with complete medium. Antigen coated beads are incubated for 24 hours at room temperature followed by extensive washing with distilled water. $^{125}$I-labeled antigen is then added (100-150,000 cpm) and the plates are incubated at room temperature for an additional 36 hr. period. The beads are then extensively washed with distilled water and counted in a Packard gamma counter. The second phase is a solid phase radioimmunoassay affinity purified goat anti-mouse F(ab')$_2$ as described by Williams et al., Cell, Vol. 12, pp. 663-673 (1977). The third phase utilizes a microhemagglutination reaction to evaluate the mAb's ability to agglutinate antigen coated human 0-negative red blood cells as described by Wands et al., Gastroenterology, Vol. 68, pp. 105-112 (1975).

Seven BVDV-specific mAb clones have been generated that neutralize both BVDV 1 and 2 in vitro (clones 2C11, 1C2, 2D7, 2H5, 1G4, 1A4, 2F12, data not shown). These mAb clones are currently undergoing a second round of cloning; once the sub-clones have been tested for BVDV neutralization, at least one mAb will be selected, characterized and the hybridoma secreting the mAb will be used to generate single chain antibody.

b) Single Chain Variable Fragment (scFv) Production

A single-chain variable fragment (scFv) is a fusion protein of the variable regions of the heavy ($V_H$) and light chains ($V_L$) of immunoglobulins, connected with a short linker peptide, typically of ten to about 25 amino acids. In some embodiments the linker is rich in glycine for flexibility, as well as serine or threonine for solubility, and can connect the N-terminus of the $V_H$ with the C-terminus of the $V_L$, or vice versa. scFv proteins retain the specificity of the original immunoglobulin, despite removal of the constant regions and the introduction of the linker. scFv fragments lack the constant Fc region found in complete antibody molecules, and, thus, the common binding sites used to purify antibodies.

A variety of methods for producing a scFv that targets a specific antigen are known to those skilled in the art. A first method requires generating a mouse hybridoma clone (using the methods above) followed by isolating cDNA from the hybridoma and then amplifying the genes encoding the variable heavy ($V_H$) and variable light chains ($V_L$) of the immunoglobulin by PCR. The gene encoding the $V_H$ and the $V_L$ chains are then fused in-frame to create one open-reading frame. Nucleotides encoding a peptide linker are incorporated between the genes encoding the $V_H$ and the $V_L$ chains for flexibility and the resultant chimeric gene is sub-cloned into a protein expression vector (for example, bacterial expression vectors or eukaryotic expression vectors such as yeast) for the scFv production. A second method requires creating a scFv phage display library using cDNA from a hybridoma secreting a specific mAb, which is then screened with an antigen of interest. A third method is to screen a premade scFv antibody phage display library with an antigen of interest to identify scFv clones directly.

Divalent (or bivalent) single-chain variable fragments may be engineered by linking two scFvs. In one embodiment, this may be accomplished by producing a single peptide chain with two $V_H$ and two $V_L$ regions, yielding tandem scFvs. In another embodiment, scFvs are generated with linker peptides that are too short for the two variable regions to fold together (about five amino acids), thereby forcing the scFvs to dimerize to form a diabody. Diabodies have been shown to have dissociation constants up to 40-fold lower than corresponding scFvs, meaning that they have a much higher affinity to their target. Consequently, diabody drugs may be administered at much lower concentrations than other therapeutic antibodies while remaining capable of highly specific antigen targeting in vivo.

II. DC Recruitment

Flt3L and GM-CSF have been shown to increase DC recruitment to the intradermal immunization site. Quantitative immunohistochemistry using anti-CD1 mAb TH97A demonstrates that Flt3L and GM-CSF enhance DC recruitment to the skin (FIG. 1). Cryostat section from a pre-inoculation biopsy probed with mAb TH97A (1A); section from a day 10 biopsy probed with mAb TH97A (1B); section from a day 10 biopsy probed with an isotype-matched negative control mAb (1C); a day 10 biopsy section probed with secondary biotinylated goat anti-mouse mAb (1D), Enhanced DC recruitment was observed in all calves treated with the plasmid DNA encoding Flt3L/GM-CSF and was significantly increased (p<0.05) as compared to calves identically inoculated but with the empty vaccine vector (69).

III. Binding of Bovine CD205-Specific rscFv to Skin DCs

FIG. 2 demonstrates that the CD205-specific rscFv (produced from a hybridoma that secretes mAb CC98) is able to target antigen to bovine DCs in situ. The binding of bovine CD205-specific rscFv to skin DCs was examined by immunohistochemistry using cryostat sections from a skin biopsy. Cryostat sections were probed with a monoclonal antibody secreted by the hybridoma that was used to generate the rscFv (2A); Cryostat section probed with the rscFv fused to an antigen (MSP1) (2B); Cryostat section probed with an isotype control scFv-MSP1 chimera (2C); and, cryostat section probed with an isotype-matched control mAb (2D) (70).

IV. Immunization of Neonatal Calves with a DNA Vaccine

Figure 3A:
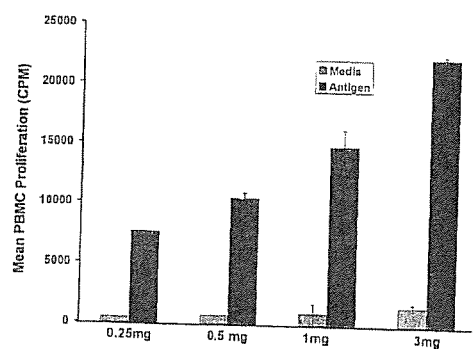
Figure 3B:
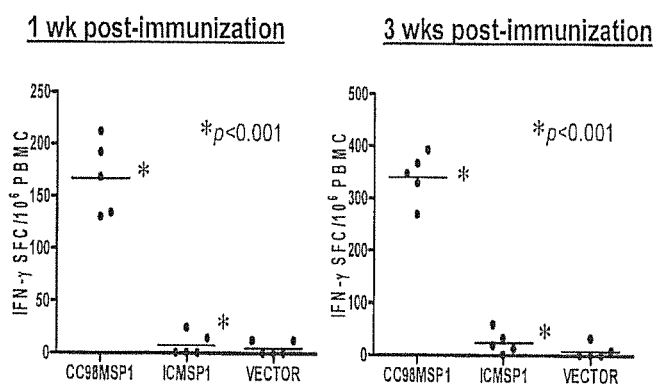

Results demonstrate that immunization of calves with a single dose of a DNA vaccine capable of DC recruitment, CD205 antigen targeting and CD40L-directed DC activation was able to prime and expand robust IFN-$\gamma^+$CD4$^+$ T cell responses that undergo rapid recall upon boost (70). FIG. 3A demonstrates that immunization with a single dose of a DNA vaccine designated CC98MSP1, encoding a DC-targeted A. marginale MSP1 antigen and DNA expressing Flt3L/GM-CSF/CD40L, primes rapid T cell response. A dose-escalation (0.25-3 mg) experiment was conducted using DRB3*1101-matched calves (n=1) to determine the minimal dose of the CC98MSP1 DNA vaccine required to prime T cell responses following a single inoculation. The calves were inoculated (Id) with a mixture of the CC98MSP 1 DNA vaccine, and the DNA-encoded Flt3L/GM-CSF/CD40L (0.5 mg each). MSP1-specific T cell responses were tested 1 week PI by proliferation assay using fresh PBMCs (69). FIG. 3B demonstrates that immunization of calves with a single dose of a DNA vaccine capable of DC recruitment, CD205 antigen targeting and CD40L-directed DC activation, primed and expanded robust IFN-$\gamma^+$CD4$^+$ T cell responses. DRB3*1101-matched calves (n=5) were immunized intradermally with the CC98MSP1 DNA vaccine (0.25 mg), a control (ICMSP1), or empty plasmid (vector) mixed with DNA-encoding Flt3L/GM-CSF/CD40L (0.5 mg each). MSP1-specific IFN-$\gamma$+CD4+ T cell responses were tested by ELISPOT assay using fresh PBMCs (69).

V. Cytokine Expression by Recombinant Adenoviruses.

Figure 5:
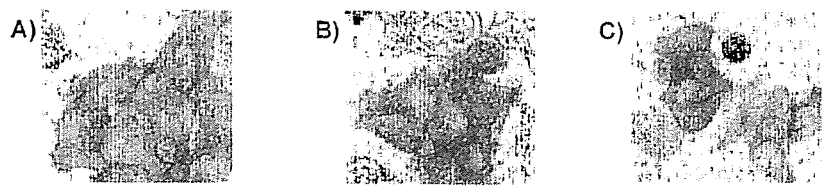

Recombinant adenoviruses encoding bovine Flt3L, GM-CSF, or CD40L were generated using ViraPower Adenoviral Gateway Expression Kit (Invitrogen) according to the manufacturer's instructions. FIG. 5 demonstrates that the recombinant adenoviruses (designated AdFlt3L, AdGM-CSF, and AdCD40L) express the encoded cytokines. Cytokine expression was tested by immunocytochemistry using 293A cells. Briefly, rAdFlt3L-infected cells were probed with soluble human Flt3-Fc receptor (5A); rAdGM-CSF-infected cells were probed with mAb GM-CSF 20.1 (5B); and 293A cells were infected with the rAdCD40L-infected cells probed with anti-FLAG mAb (5C). Cells infected with a rAd-luciferase (Adluc) served as a negative control. The biological activity of the expressed Flt3L, GM-CSF, and CD40L was confirmed as previously described (69, 87, 88). In one embodiment of the present invention, recombinant adenoviruses such as AdFlt3L, AdGM-CSF, and AdCD40L may be used to enhance in vivo DC recruitment as indicated by the ability of Flt3L and GM-CSF to increase DC recruitment to the intradermal immunization site (FIG. 1).

VI. Generation of Bovine CD205-Specific scFv

A recombinant bovine CD205-specific scFv for DC-targeting and a scFv from an isotype-matched control mAb were generated in 293 Free-style cells (Invitrogen). The scFv is a mouse IgG ($V_H$-$V_L$ chimera) but most of the amino acids in the $V_H$ chain and the whole $V_L$ chain may be replaced with bovine IgG residues without compromising function (89). Briefly, the ORFs of the $V_H$ and $V_L$ chains of the mAb CC98 (IgG2b) were amplified from the CC98 hybridoma (90) cDNA by separate asymmetric PCR (91) using a Mouse ScFv Module (Amersham) according to the manufacturer's instructions.

The asymmetric PCR products were joined by overlap extension PCR (91), resulting in the CC98 scFv containing the $(G_4S)_3$ (SEQ ID NO: 4) linker between the $V_H$ and the $V_L$.

Similarly, a control scFv, designated IC scFv, was constructed using cDNA generated from a hybridoma that secretes an isotype-matched mouse IgG2b mAb. To test CD205 binding, FLAG-tagged recombinant CC98 scFv, a rCC98 scFv fused to a 30 kDa protein (MSP1), and the rIC scFv control was expressed in 293 Free-Style cells (Invitrogen) and affinity purified using anti-FLAG agarose resin (Sigma).

Figure 6:
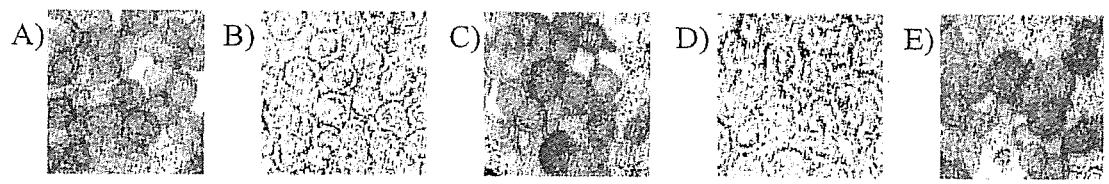

Binding of FLAG-tagged rCC98 scFv to bovine CD205 receptor was tested by immunocytochemistry using 293-F cells transfected with a construct (pCD205) encoding bovine CD205 receptor (90) (FIG. 6). Briefly, pCD205 transfected 293-F cells were probed with recombinant CC98 scFv (6A); pCD205 transfected 293-F cells were probed with the negative control recombinant IC scFv (6B); pCD205 transfected 293-F cells were probed with the mouse anti-bovine CD205 mAb CC98 (6C); pCD205 transfected 293-F cells were probed with an isotype-matched control mAb (6D); and pCD205 transfected 293-F cells were probed with recombinant CC98MSP1 protein (6E). Cell monolayers for panels A, B and E were probed with anti-FLAG AP-conjugated mAb, whereas panels C and D were probed with anti-mouse AP-conjugate (70). Results demonstrate that the rCC98 scFv, but not the rIC scFv, binds bovine CD205 (FIG. 6A-D). In fact the rCC98 scFv is as capable of binding CD205 as the anti-CD205 mAb. The CC98 scFv retains CD205 binding after in-frame addition of unrelated sequences (FIG. 6E) and the CC98 scFv, but not the rIC scFv, binds bovine DCs in situ (FIG. 2) (70).

VII. Generation of the CC98-348 Bi-Specific Diabody

A diabody (designated CC98-348) containing the CD205-specific CC98 scFv fused in-frame to a BVDV E2 antigen-specific scFv (generated from mAb 348) that neutralizes BVDV 1 and 2 (79) was generated to both mask MLV vaccines against BVDV 1 and 2 and target DCs. In addition to mAb 348, other BVDV neutralizing mAbs are currently being developed to allow the production of additional bi-specific diabodies. Several promising clones are currently being screened for neutralization of BVDV1&2 (i.e. clones 2C11, IC2, 2D7, 2H5, 1G4, 1A4, 2F12).

Figure 7:
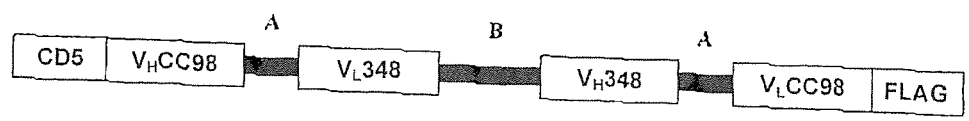

FIG. 7 depicts the structure of the CC98-348 single chain diabody.

The N-terminal CD5 secretory signal sequence, arrangement of the variable domains as well as the linker sequences A (G$_4$S) (SEQ ID NO: 2) and B (G$_4$SG$_2$RASG$_4$SG$_4$S) (SEQ ID NO: 3), and the C-terminal FLAG tag are shown.

The structure of the negative control diabody (designated IC-348) is similar but with V$_H$ and V$_L$ domains from an isotype-matched control scFv. A second negative control diabody for the 348 scFv (designated IC-IR) was also generated.

The V$_H$ and V$_L$ fragments of the CC98 scFv and the cDNA encoding the mAb 348 (79) were amplified by separate asymmetric PCR (91) using a Mouse ScFv Module (Amersham). The asymmetric PCR products were joined in-frame by overlap extension PCR (91) in the format V$_H$CC98$_{linkerA}$V$_L$348$_{linkerA}$V$_H$348$_{linkerA}$V$_L$CC98 (FIG. 7), where linkerA is G$_4$S (SEQ ID NO: 2) and linkerB is G$_4$SG$_2$RASG$_4$SG$_4$S (80) (SEQ ID NO: 3), to generate a chimeric gene designated cc98-348.

This chimeric gene was modified to contain a 5' linked eukaryotic secretory signal (designated CD5ss) (69, 86) and a 3' linked sequence encoding a FLAG-tag. The resultant chimeric gene (designated cd5cc98-348flag) was used to generate a recombinant adenovirus (designated AdCC98-348) for expression of recombinant CC98-348 in 293 Free-style cells (Invitrogen). Expression of the recombinant CC98-348 diabody was verified by immunocytochemistry using anti-FLAG mAb (Sigma) and the protein is affinity purified using anti-FLAG agarose gel (Sigma). Similarly, the V$_H$ and V$_L$ fragments from the IC control scFv were fused in-frame with the 348 scFv or an irrelevant scFv to generate control diabodies (designated IC-348 and IC-IR, respectively). Binding of the CC98-348 diabody to bovine CD205 was verified by immunocytometric analysis of 293 F cells transfected with pCD205. CC98 mAb is the positive control whereas the IC-348 and the IC-IR diabodies serve as negative controls. Binding of the CC98-348 and the IC-348 diabodies to BVDV was verified by ELISA. The mAb 348 served as a positive control, whereas an isotype-matched mAb and the IC-IR diabody served as negative controls.

VIII. Generation of Adenoviruses Expressing BVDV Antigens

Resolution of acute BVDV infection requires cell-mediated immunity. The N$^{pro}$, capsid, E$^{ms}$, E2, and NS2-3 antigens of BVDV contain B and T cell determinants that confer protection against infection with wt virus (20, 22, 23, 26-28). Since significant portions of the N$^{pro}$, capsid, E$^{ms}$, E2, and NS2-3 antigens are highly conserved among BVDV strains they represent ideal targets for protection against multiple BVDV strains (32).

Recombinant adenoviruses expressing chimeric BVDV antigens will be generated using the ViraPower Adenoviral Gateway Expression Kit (Livitrogen). This vector is replication-incompetent in non-complementing cell lines due to deletion of the E1 and E3 genes but replicates to $10^{12}$ pfu/ml in complementing cells (33). The vector can accommodate up to 7.5 kb of foreign DNA and utilizes the human CVM promoter to drive high level transgene expression (33). Hydrophilic domains of the N$^{pro}$-capsid (amino acids 1-252), E$^{ms}$-E1 (amino acid 270-564), and the E2 antigen (amino acids 693-1035) from currently sequenced BVDV type 1 or type 2 were aligned and the consensus amino acid sequences used to design broadly representative mosaic chimeric polypeptides, designated BVDV1$_{NcapE2}$ and BVDV2$_{NcapE2}$, respectively. The mosaic chimeric polypeptides sequences have been used to generate codon-optimized synthetic genes (for optimal protein expression in bovine cells in vivo) and these genes have been modified to contain the gene encoding the CC98 scFv for DC-targeting at the 5' end the gene encoding FLAG tag at the 3' end (69, 86) Initial results from expression constructs (DNA and adenovirus) bearing the chimeric genes demonstrate the ability to express CD205-targeted antigen; experiments to optimize protein expression are currently being performed. The resultant chimeric genes have been used to generate recombinant adenoviruses, designated AdCC98-BVDV1$_{NcapE2}$ and AdCC98-BVDV2$_{NcapE2}$, respectively. FIG. 8A depicts the structure of the CC98-BVDV1$_{NcapE2}$ chimera. The CD5 secretory signal sequence, arrangement of the CC98 variable domains, linker sequences A (G$_4$S) (SEQ ID NO: 4) and B (G$_4$S) (SEQ ID NO: 2), hydrophilic domains of N$^{pro}$, capsid, and the FLAG tag are shown.

The structure of the control chimeras, IC-BVDV1$_{NcapE2}$ and IC-BVDV2$_{NcapE2}$, are similar but with the IC variable domains. Similarly, an adenovirus, designated AdCC98-BVDV1$_{NS2-3}$ and AdCC98-BVDV2$_{NS2-3}$, respectively, have been generated using the hydrophilic domains of the NS2-3 antigens (amino acids 1300-2384). FIG. 8B depicts the structure of the CC98-BVDV1$_{NS2-3}$ chimera. The structure of the control chimeras are similar but with the IC variable domains. FIG. 9 depicts the hydropathic profiles of the BVDV chimeric proteins—CC98-BVDV1$_{NcapE2}$ chimera (9A); and CC98-BVDV1$_{NS2-3}$ chimera (9B). The hydropathic profiles of the control chimeras (IC-BVDV1$_{NcapE2}$ and IC-BVDV1$_{NS2-3}$ are similar to the CC98-BVDV1$_{NcapE2}$ and CC98-BVDV1$_{NS2-3}$ chimeras, respectively. Conserved regions of these hydrophilic domains are rich in MHC DR-restricted T cell epitopes (28), and in the closely related Classical swine fever virus, highly conserved protective CD4$^+$ T$_H$ cell and CD8$^+$ CTL epitopes have been defined within the same regions (110, 111).

Protein expression was verified by immunocytochemistry using anti-FLAG mAb (Sigma) and BVDV-specific mAbs and polyclonal antibodies. CD205 binding was verified by immunocytometric analysis of 293A cells transfected with the pCD205 construct. Processing and presentation of the antigens expressed by these adenoviruses was verified by $^3$H-thymidine incorporation and cell cytotoxicity using BVDV-reactive PBMCs.

IX. Protection and DC Targeting of the MLV BVDV Vaccine

Efficacy of MLV BVDV vaccine virus protection against neutralization by BVDV-specific antibodies and DC targeting by the CC98-348 diabody was evaluated in vitro. To evaluate efficacy of the CC98-348 diabody to protect the BVD virus from complement-6 mediated lysis, 4×10$^6$ TCID$_{50}$ of a commercial MLV vaccine against BVDV 1 and 2 was incubated at 37° C. for 1 hr with either the CC98-348 or IC-348 diabodies in the presence or absence of BVDV-specific neutralizing antibodies in medium containing non-inactivated bovine serum to preserve complement activity. The mixture was then added to 293A cell monolayers (BVD virus does not infect 293A cells) transfected with bovine CD205 or non-transfected cells as controls. The monolayers were incubated at 37° C. for 1 hr to allow binding of the CC98 to CD205, washed to remove unbound complexes and pH 3.5 growth medium was added for 10 minutes to free the diabody-protected virus bound to CD205 transfected 293A cells. The medium, free of 293A cells, was recovered and added to MDBK cell monolayers to support BVDV replication and the pH was adjusted to 7.4. The MDBK monolayers were incubated for 6 hrs, washed, and normal growth medium added. After three days the presence of BVDV in the MDBK cells was evaluated by immunocytometric analysis using mAb 348 (94). In one embodiment of the present invention, it is expected that incubation of BVDV with CC98-348 or IC-348 diabody, but not with BVDV neutralizing antibodies, will result in protection of BVD virus but only CC98-348 is expected to protect and target the virus to CD205 as evidenced by the detection of virus in MDBK cells.

X. CC98-348 Mediated Targeting, Binding and Protection

The ability to demonstrate that the CC98-348 conjugate targets BVDV to CD205 and inhibits binding of a FITC-labeled anti-BVDV polyclonal antibody is critical evidence for proof of concept. Results demonstrate that the CD205-BVDV E2-specific diabody coat MLV vaccine virions and protect the vaccine from antibody-mediated complement lysis while also targeting the coated virions to DCs. In one embodiment of the present invention, this bi-functional capability dramatically improves the efficacy of current BVDV MLV vaccines in neonatal calves.

The bi-specific CC98-348 diabody consists of the bovine CD205-specific mAb CC98 conjugated to the BVDV neutralizing mAb 348 (Deregt, D., et al 1998. *Virus Research* 53:81-90). FIGS. 11-13 demonstrate that the CC98-348 diabody is bi-functional due to its ability to: 1) target the CC98-3348 conjugate to bovine CD205 (FIG. 10); 2) binds to BVDV (FIG. 11); 3) target BVDV to CD205 (FIGS. 12) and 4) protect BVDV from destruction by anti-BVDV polyclonal antibody (FIG. 12, and data not shown).

Figure 10:
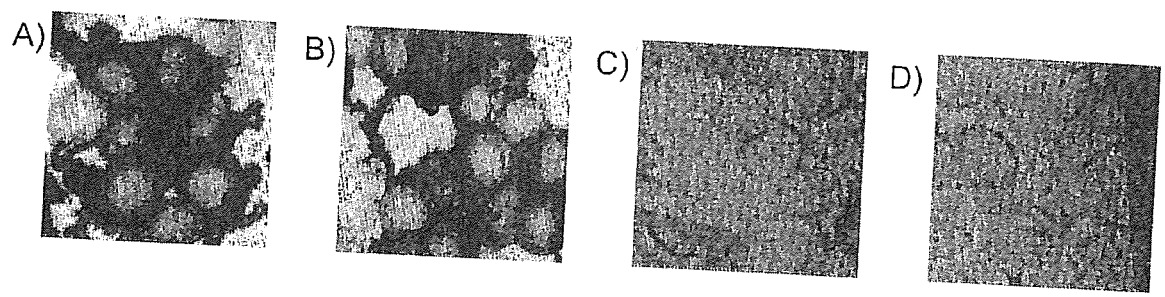
FIG. 10 depicts binding of the CC98-343 antibody conjugate to bovine CD205. 293A cells transfected with bovine CD205 were probed with mAb CC98 (IgG2b) (10A); CC98-343 conjugate (10B); mAb 348 (10C); and IgG2b isotype-matched negative control mAb (10D).
Figure 11:
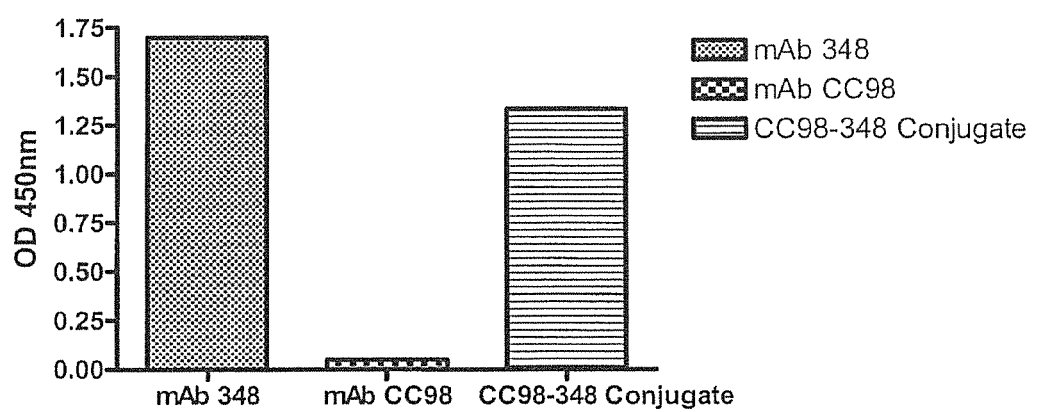
FIG. 11 depicts an ELISA evaluating the binding of the CC98-348 conjugate to cytopathic, non-cytopathic and commercial BVDV vaccines.

The ability of the CC98-348 conjugate to bind to CD205 was demonstrated by immunocytometric analysis of cells that express CD205 (FIG. 10). Briefly, 293A cells were transfected with bovine CD205 and then probed with mAb CC98 (IgG2b) (A), CC98-348 conjugate (B), mAb 348 (C) and IgG2b isotype-matched negative control mAb (D). The ability of the CC98-348 conjugate to bind BVDV was demonstrated by ELISA (FIG. 11). Results indicate that the CC98-348 conjugate binds to both cytopathic and non-cytopathic BVDV and to a commercial BVDV vaccine.

The ability to target BVDV to CD205 by the CC98-348 conjugate was also demonstrated by immunocytochemistry (FIG. 12). Briefly, the CC98-348 conjugate was pre-incubated with BVDV to allow binding of the virus to the 348 portion of the conjugate and this mixture was then layered on CD205-transfected 293A cells and incubated for 1 hr (12A). Note that BVDV does not infect 293A cells (human embryonic kidney cells). Following extensive washes, the CC98-348 conjugate plus virus was eluted with low pH buffer and immediately transferred to MDBK cell monolayers, which are permissive to BVDV infection and support virus growth. The pH was raised to allow virus to attach to the MDBK cells. It is contemplated that this step allows the CC98-348 conjugate to compete with the MDBK cells for the virus as the pH was raised but the virus taken up by the cells replicated over three days and were detectable following staining of the MDBK cell monolayers with mAb 348 (12A). The negative control was similarly treated except that unconjugated mAbs CC98 and 348 were used (B); the positive control (BVDV) was subjected to the same pH treatment (C). To test whether the CC98-348 conjugate protects BVDV from binding of anti-BVDV polyclonal antibody, CD205 transfected 293A cells were treated as in A above and following extensive washes, FITC-labeled anti-BVDV polyclonal antibody was added and the cells evaluated by FACS. Binding of the CC98-348 conjugate to BVDV completely inhibited binding of the FITC-labeled anti-BVDV polyclonal antibody (Data not shown). To test whether the CC98-348 conjugate protects the BVDV from anti-BVDV antibody-directed complement lysis, BVDV was masked using the CC98-348 conjugate and the mixture subjected to rabbit complement in the presence of anti-BVDV polyclonal antibody. BVDV mixed with negative control conjugate, CC98, or 348 served as the controls. This assay is not critical since we have shown that the CC98-348 conjugate completely inhibited binding of anti-BVDV polyclonal antibody to BVDV.

XI. Protective Immunity in Neonatal Calves Vaccinated with an Adenovirus Expressing Flt3L/GM-CSF/CD40L Mixed with a DC-Targeted MLV Vaccine Against BVDV One embodiment of the present invention contemplates priming protective immunity in neonatal calves by immunizing with a single dose of adenoviruses expressing Flt3L/GM-CSF/CD40L mixed with a DC-targeted MLV vaccine against BVDV 1 and 2.

We have generated a bovine CD205-specific scFv (designated CC98) for DC-antigen targeting and an isotype-matched control scFv (FIG. 2), (designated IC), and shown that immunization of calves with a single dose of a DNA vaccine capable of DC recruitment, CD205 antigen targeting and CD40L-directed DC activation, primed and expanded robust IFN-$\gamma^+$CD4$^+$ T cell responses (FIG. 3A-B) that underwent rapid recall upon boost (70). A diabody (designated CC98-348) containing the CD205-specific CC98 scFv (FIG. 2) fused in-frame to a BVDV E2 antigen-specific scFv generated from a monoclonal antibody, mAb 348, that neutralizes BVDV 1 and 2 (79) will be generated for masking a MLV vaccine against BVDV 1 and 2, and for DC targeting (FIG. 4). A negative control diabody (designated IC-348) will similarly be generated but with a scFv from an isotype-matched control mAb (FIGS. 2 and 6). A control scFv for the 348 scFv will be used to generate a second negative control diabody, designated IC-IR.

Generation of functional CD4$^+$ T helper and CD8$^+$ CTLs requires DC activation through CD40 signaling and increases production of pro-inflammatory cytokines and Th1 differentiation (67, 74, 75) (76). Importantly, DC activation through CD40 signaling overcomes tolerance and may release immature DCs from the control of regulatory CD4$^+$CD25$^+$ T cells (77). The recombinant adenovirus, AdCD40L, expressing bovine CD40L (FIG. 5) will be used for enhancing DC activation. The potential of AdFlt3L/AdGM-CSF-dependent DC recruitment, AdCD40L-mediated DC activation, and CC98-348-directed masking of a MLV vaccine against BVDV 1 and 2 and DC targeting to enhance priming of protective BVDV-specific CD4$^+$ T helper and CD8$^+$ CTL responses in the presence of neutralizing antibodies will be evaluated in neonatal calves as described below.

a) Immunization of Neonatal Calves

Five groups (n=5) of age-matched neonatal calves with protective BVDV neutralizing antibody titers were used in the present study (15). A herd of greater than 6,000 animals comprising young (1 week to 4 months old) Holstein calves (StoneyPoint AgriCorp, Melissa, Tex.) was used to select age-matched calves following screening for BVDV neutralizing antibody titers as previously described (97). Group size was estimated using IFN-$\gamma^+$CD4$^+$ T cell response data from calves primed with a single dose of a DNA vaccine capable of DC recruitment, CD205 antigen targeting and CD40L-directed DC activation. The treatment group for that study was composed of DRB3*1101-matched calves (n=5) immunized with a single dose of the CC98MSP1 DNA vaccine (0.25 mg) encoding a DC-targeted A. marginale MSP1 antigen mixed with DNA constructs expressing FIT3L/GM-CSF/CD40L (0.5 mg each) (FIG. 3B) (70). The control group was composed of DRB3*1101-matched calves (n=5) that were similarly immunized but with a DNA vaccine, ICMSP1, encoding a non-DC-targeted MSP1 antigen (FIG. 3B). The mean MSP1-specific IFN-γ$^-$CD4$^+$ T cell response for the treatment (n=5) and control groups (n=5) 1 week post-immunization were 167.2±35.74 and 7.600±10.99, respectively (FIG. 3B) (70). Based on this difference, the probability of rejecting the null hypothesis of no difference between the treatment and control mean IFN-γ$^+$CD4$^+$ T cell responses for a sample of n=5 per treatment is 0.9 (p=0.001). Assuming that a similar difference in BVDV-specific IFN-γ$^+$CD4$^+$ T cell responses is detected between calves primed with a single dose of the CC98-348-protected and DC-targeted MLV vaccine against BVDV 1 and 2 (designated CC98-348$_{BVDV}$) and the control calves immunized with the IC-348-protected but non-targeted vaccine (IC-348$_{BVDV}$), then significant differences between the treatment and control groups may be detected by using five calves per group.

Each calf in group A was inoculated intradermally with 5×10$^9$ TCID$_{50}$ of the CC98-348$_{BVDV}$ vaccine mixed with the AdFlt3L/AdGM-CSF/AdCD40L (5×10$^9$ pfu/each). The 5×10$^9$ pfu dose of a recombinant adenovirus has been shown to be effective in cattle (98). Each calf in groups B and C similarly inoculated with the IC-348$_{BVDV}$ vaccine or with a non-protected and non-targeted BVDV vaccine (IC-IR$_{BVDV}$), respectively. Calves in group D are inoculated with the CC98-348$_{BVDV}$ vaccine, as in group A, but mixed with the Adluciferase virus to serve as a control for the cytokines. Negative control calves in group E were inoculated with the cytokine adenoviruses, as in group A, but mixed with an equivalent amount of the CC98-348 diabody used in the CC98-348$_{BVDV}$ vaccine.

b) Analysis of Immune Responses

Following immunization, peripheral blood mononuclear cells (PBMCs) were used to evaluate T cell responses, whereas serum used to evaluate antibody responses and virus neutralization. BVDV-specific IFN-γ$^+$CD4$^+$ and IFN-γ$^+$CD8$^+$ T cells, CD4$^+$ T cell proliferation, CD8$^+$ T cell cytotoxicity and antibody responses induced by the vaccine immunization was evaluated by IFN-γ$^+$ ELISPOT, $^3$H-thymidine incorporation, cell-mediated cytotoxicity assay (using autologous BVDV 1- or 2-infected ConA stimulated lymphoblasts as targets), ELISA, and BVDV neutralization assays, respectively, as previously described (22, 97, 99). These parameters were tested bi-weekly to determine the post-vaccination interval required to detect statistically significant BVDV-specific immune responses. The significance of any differences in BVDV-specific immune responses between treatment group A (Ad-cytokines/CC98-348$_{BVDV}$) and the control groups B (Ad-cytokines/IC-348$_{BVDV}$); C (Ad-cytokines/IC-IR$_{BVDV}$); D (Adluc/CC98-348$_{BVDV}$); and E (Ad-cytokines/CC98-348) was analyzed using ANOVA.

c) Analysis of Recall Responses and Protection

Following the decline of neutralizing antibodies to below protective titers in the negative control calves (group E), which occur at approximately 6-8 months (15), live challenge was used to determine efficacy of the Ad-cytokine/CC98-348$_{BVDV}$ vaccine. All calves were challenged by intranasal inoculation with 5×10$^6$ TCID$_{50}$ of BVDV (NY-1 noncytopathic strain) and then evaluated for clinical and hematological parameters, and viremia as previously described (97). Any reactions to the challenge were calculated as a disease reaction index based on a previously described combination of viremia, clinical and hematological parameters (100). One-week post challenge, BVDV-specific antibody titers, virus neutralization, and T cell responses was evaluated. The significance of the differences in BVDV-specific immune responses and disease indices between treatment group A (Ad-cytokines/CC98-348$_{BVDV}$) and the control groups B (Ad-cytokines/IC-348$_{BVDV}$); C (Ad-cytokines/IC-IR$_{BVDV}$); D (Adluc/CC98-348$_{BVDV}$) and E (Ad-cytokines/CC98-348) was analyzed using ANOVA.

XII. Protective Immunity in Neonatal Calves Vaccinated with an Adenovirus Expressing Flt3L/GM-CSF/CD40L Mixed with DC-Targeted BVDV Antigens There is a need for alternative BVDV vaccines that are efficacious, safe, cost-effective, and non-susceptible to BVDV-specific antibody neutralization. One embodiment of the present invention contemplates priming protective immunity in neonatal calves by immunizing with a single dose of adenoviruses expressing Flt3L/GM-CSF/CD40L (for DC recruitment and activation) and DC-targeted protective BVDV antigens. In one embodiment, the immunization induces robust effector/memory CD4$^+$ and CD8$^+$ T cell responses to prime and expand cell-mediated immunity in the presence of neutralizing antibodies.

a) Immunization of Neonatal Calves

Four groups (n=5) of age-matched neonatal calves with protective colostrum-derived BVDV neutralizing antibody titers were used in this study. Group size was estimated using MSP1-specific IFN-γ$^+$CD4$^+$ T cell response data (FIG. 3B) (70). Based on the difference between the treatment and the control mean MSP1-specific IFN-γ$^+$CD4$^+$ T cell responses (FIG. 3B), the probability of rejecting the null hypothesis of no difference between the treatment and the control mean IFN-γ$^+$CD4$^+$ T cell responses for a sample of n=5 per treatment is 0.9 (p=0.001). Assuming that a similar difference in BVDV-specific IFN-γ$^+$CD4$^+$ T cell responses between calves primed with a single dose of the vaccine formulation containing adenoviruses expressing the DC-targeted BVDV antigens and the control calves immunized with non-DC-targeted antigens is detected, a significant difference between the treatment and the control groups can be detected by using five calves per group. Calves are immunized as summarized in FIG. 13.

Briefly, calves in groups A and C will be inoculated intradermally with a single dose of the adenoviruses expressing the DC-targeted BVDV antigens (5×10$^9$ pfu/each) mixed with either the adenoviruses expressing the cytokines (5×10$^9$ pfu/each) or the Adluciferase control, respectively. Calves in group B will be inoculated similarly, but with a mixture of the adenoviruses expressing the non-targeted BVDV antigens mixed with the adenoviruses expressing the cytokines. Calves in group D will receive the Adluciferase mixed with the adenoviruses expressing the cytokines.

b) Analysis of Immune Responses

Following immunization, PBMCs were used to evaluate T cell responses and sera was used to evaluate antibody responses and virus neutralization. BVDV-specific IFN-γ$^+$CD4$^+$ and IFN-γ$^+$CD8$^+$ T cells, CD4$^+$ T cell proliferation, CD8$^+$ T cell cytotoxicity and antibody responses was evaluated by IFN-γ$^+$ELISPOT, $^3$H-thymidine incorporation, cell-mediated cytotoxicity assay, ELISA, and BVDV neutralization assays, respectively. These parameters were tested bi-weekly to determine the post-vaccination interval required to detect statistically significant BVDV-specific immune responses. The significance of the differences in BVDV-specific immune responses between treatment (group A) and the controls (groups B-D) was analyzed using ANOVA.

c) Analysis o(Recall Responses and Protection

Following decline of neutralizing antibodies to below protective titers (6-8 months) in the negative control calves (group D), live challenge was used to determine the efficacy of the vaccine formulation containing the adenoviruses expressing the DC-targeted BVDV antigens and the cytokines. All calves were challenged as described above. Disease indices, BVDV-specific antibody titers, virus neutralization, and T cell responses were evaluated as described above. The significance of the differences in disease indices and BVDV-specific immune responses between the treatment (group A) and the controls (groups B-D) was analyzed using ANOVA.

XIII. Potential Outcomes and Alternative Strategies a) BVDV Vaccine Protection and DC Targeting In one embodiment, the present invention contemplates testing whether CC98-348 diabody-dependent BVDV vaccine protection and DC targeting, and the AdFlt3L/AdGM-CSF/AdCD40L-directed DC recruitment and activation, significantly enhances priming and expansion of BVDV-specific B and T cell responses in the presence of neutralizing antibodies and confers protection upon challenge.

The AdFlt3L/AdGM-CSF/AdCD40L viruses efficiently express functional cytokines (FIG. 5A-C) that may serve as a potent adjuvant and significantly enhance priming and expansion of BVDV-specific immunity in neonatal calves in the presence of neutralizing antibodies. Such an outcome would be consistent with previous demonstrations that Flt3L, GM-CSF, and CD40L are potent molecular adjuvants that enhance DC recruitment, activation, and vaccine efficacy in cattle (FIGS. 1 and 3), humans, and mice (69, 70, 72, 76, 77, 92, 93). Comparison of immune responses between group A (Ad-cytokines/CC98-348$_{BVDV}$) and group D (Ad-luc/CC98-348$_{BVDV}$) should reveal whether the Flt3L/GM-CSF/CD40L cytokines will enhance priming and expansion of BVDV-specific immune responses in neonatal calves in the presence of neutralizing antibodies. Should the adenovirus-expressed cytokines fail to significantly enhance priming of BVDV-specific immune responses, an alternative strategy for augmenting the immunogenicity of the CC98-348$_{BVDV}$ vaccine is to determine whether addition of graded amounts of TLR 3 ligand (poly I:C), TLR 7/8 ligands (imiquimod and resiquimod), and TLR 9 (CpG ODNs) will improve vaccine efficacy (101). The Poly I:C, imiquimod and resiquimod, and CpG motifs activate innate and acquired immunity via TLR-dependent mechanism, resulting in cytokine induction and enhanced cell-mediated immunity (73, 102, 103).

The CC98 scFv binds and targets antigen to bovine CD205 in vitro and to DCs in situ (FIGS. 2 and 6) and thus the CC98-348 diabody should protect and target the BVDV vaccine virus to DC in vivo and thus enhance priming and expansion of BVDV-specific immune responses in the presence of neutralizing antibodies. This outcome will be consistent with the demonstration that targeting antigen to CD205 using anti-CD205 antibody significantly enhances T cell responses and protective cellular immunity in a mouse model (67), and primed robust IFN-γ$^+$CD4$^+$ T cell responses in cattle (FIG. 3A-B) that underwent rapid recall upon boost (70). It is possible that the 348 scFv motif alone may not fully protect the MLV BVDV vaccine virus against neutralization by antibody-mediated complement lysis and opsonization. Current efforts are focused on generating a phage-display library using spleen cDNA from a BVDV immune cow to identify a minimal number of BVDV-specific scFv that will fully protect the MLV BVDV vaccine virus against neutralization (104). These scFv will be used to generate diabodies for effective protection and DC-targeting of the MLV BVDV vaccine virus and are expected to improve vaccine efficacy in neonatal calves. Such recombinant diabodies can be produced inexpensively in bacteria expression systems and used as additives in current commercially available MLV vaccines against BVDV 1 and 2.

If, after one immunization, a significant BVDV-specific immune responses and/or protection is detected in group A (Ad-cytokines/CC98-348$_{BVDV}$) but none in group B (Ad-cytokines/IC-348$_{BVDV}$), the hypothesis that intradermal inoculation of neonatal BVDV calves with a single dose of a vaccine formulation containing adenovirus expressing Flt3L/GM-CSF/CD40L mixed with CC98-348-coated MLV vaccine against BVDV and 2 is capable of priming and expanding protective BVDV-specific immune responses in the presence of neutralizing antibody will be accepted. The hypothesis will also be accepted if, after one immunization, we detect significantly greater BVDV-specific immune responses and/or protection in group A as compared to groups B-E. Failure to detect significant BVDV-specific immune responses in group A after a single immunization will indicate that immunization of neonatal calves with a single dose of the Ad-cytokines/CC98-348$_{BVDV}$ vaccine is not sufficient to prime and expand significant BVDV-specific immune responses in the presence of neutralizing antibodies and a booster dose is required. Detection of a rapid recall response and/or significant protection after challenge in group A as compared to all the other groups (B-E), will indicate that immunization of neonatal calves with a single dose of the Ad-cytokines/CC98-348$_{BVDV}$ vaccine primed BVDV-specific immune responses in the presence of neutralizing antibodies but failed to fully expand the primed responses. Failure to detect significant BVDV-specific immune responses and/or protection in group A as compared to all the other groups (B-E) after challenge will result in the rejection of the hypothesis.

b) Immunization of Neonatal Calves

In one embodiment, the present invention contemplates testing whether immunization of neonatal calves with a single dose of a vaccine formulation containing adenoviruses expressing Flt3L/GM-CSF/CD40L for DC recruitment and activation, and DC-targeted hydrophilic domains of immunogenic BVDV antigens will prime and expand significant BVDV-specific B and T cell responses in the presence of neutralizing antibodies and confer protection upon challenge. Adenoviruses expressing the Flt3L/GM-CSF/CD40L cytokines (FIG. 5A-C) should significantly augment the immunogenicity of the adenovirus-vectored BVDV vaccine by stimulating robust DC recruitment to the immunization site (FIG. 1) (69) and activation of the BVDV antigen-loaded DCs for effective priming and expansion of protective BVDV-specific B and T cells in neonatal calves in the presence of BVDV-specific neutralizing antibodies. This is supported by previous findings, which demonstrate that Flt3L, GM-CSF, and CD40L are potent molecular adjuvants that enhance DC recruitment, activation, and vaccine efficacy in cattle (FIGS. 1 and 3), humans, and mice (69, 70, 72, 76, 77, 92, 93).

A single dose of the adenovirus-vectored BVDV vaccine should express sufficient amounts of the DC-targeted hydrophilic BVDV antigen chimeras (FIG. 9) at the DC-enriched intradermal immunization site for optimal induction and expansion of protective BVDV-specific B and T cells in neonatal calves in the presence of BVDV-specific neutralizing antibodies. This is supported by the demonstration that the replication-defective adenovirus vector directs high transgene expression (FIG. 5A-C) and augments vaccine potency in mammalian hosts through TLR-dependent and -independent DC modulation (33-35). Furthermore, immunization with a single dose of an adenovirus-vectored vaccine induces strong cytotoxic T-cell responses (36). Importantly, immunization of neonates at birth with a single dose of an adenovirus-vectored vaccine primes robust immune responses (38, 40). In addition, the CC98-directed targeting of the hydrophilic BVDV antigen chimeras (FIG. 9) to bovine DCs (FIG. 2) should significantly enhance priming and expansion of protective BVDV-specific immune responses in neonatal calves in the presence of neutralizing antibodies. This expectation is consistent with our demonstration that DC antigen targeting using the CC98 motif primed robust IFN-γ$^+$CD4$^+$ T cell responses in cattle (FIG. 3A-B) that underwent rapid recall upon boost (70).

If the adenovirus-vectored cytokines fail to significantly enhance priming of BVDV-specific immune responses, an alternative strategy for augmenting the immunogenicity of the adenovirus-vectored BVDV vaccine is to determine whether replacing the AdCD40L with an adenovirus-vectored CD40 agonistic diabody generated from an anti-bovine CD40 agonistic mAb will improve vaccine immunogenicity (75). Agonistic anti-bovine CD40 mAbs have been generated and are currently being characterized. A second alternative strategy for augmenting BVDV vaccine immunogenicity is to use TLR 3 ligand (poly I:C), TLR 7/8 ligands (imiquimod and resiquimod), and TLR 9 (CpG ODNs) to improve vaccine efficacy (101).

The hypothesis that intradermal inoculation of neonatal calves with a single dose of a vaccine formulation containing adenoviruses expressing Flt3L/GM-CSF/CD40L and DC-targeted BVDV antigens will prime and expand significant BVDV-specific B and T cell responses in the presence of neutralizing antibodies and confer protection upon challenge will be accepted if, after one immunization, a significant BVDV-specific immune responses and/or protection is detected in group A but none in group B (FIG. 13). The hypothesis will also be accepted if, after one immunization, a significantly greater BVDV-specific immune responses and/or protection is detected in group A as compared to groups B-D. Failure to detect significant BVDV-specific immune responses in group A after a single immunization will demonstrate that immunization of neonatal calves with a single dose of the Ad-cytokines/CC98-BVDV vaccine is not sufficient to prime and expand significant BVDV-specific immune responses in the presence of neutralizing antibodies and a booster dose is required. Detection of a rapid recall response and or significant protection after challenge in group A as compared to all the other groups (B-D) will demonstrate that immunization of neonatal calves with a single dose of the Ad-cytokines/CC98-BVDV vaccine primed BVDV-specific immune responses in the presence of neutralizing antibodies but failed to fully expand the primed responses. Failure to detect significant BVDV-specific immune responses and or protection in group A as compared to all the other groups (B-D) after challenge will result in the rejection of the hypothesis.

In one embodiment, the present invention contemplates two alternative strategies for further improving the proposed BVDV vaccine: 1) addition of defined DR-restricted T cell epitopes (QGGISSVDIIVTAGKDLLV (SEQ ID NO: 6), VTASGTPAFFD LKNLKGW (SEQ ID NO: 7), VEYSYIFLDEYHCATPEQ (SEQ ID NO: 8), CATPEQLAIIGKIHRFSE (SEQ ID NO: 9), MKGNMLVFVPTRNMAVEV (SEQ ID NO: 10), GRVKPGRYYRSQETA (SEQ ID NO: 11), NGEVTDTYENYSFLNARK (SEQ ID NO: 12)) (28) from the conserved regions of the E2 and NS2-3 antigens from BVDV 1a and variants of these epitopes from the other BVDV genotypes to the BVDV antigen chimeras to generate a synthetic chimeric gene encoding a BVDV polyepitope; and 2) use short-term T cell lines from BVDV vaccinates and or convalescent animals to identify CTL epitopes from the pool of potential WIC class I allele-specific cytotoxic T cell peptide motifs from the BVDV polyprotein and reactive epitopes will be added to the BVDV polyepitope to generate a CD4$^-$ and CD8$^-$ epitope-rich vaccine candidate (28, 31).

We claim:

1. A method, comprising:
   a) providing;
      i) a subject at risk for infection by a virus,
      ii) a mosaic chimeric viral vaccine particle comprising an $N^{pro}$ antigenic site derived from bovine viral diarrhea virus (BVDV) 1 or BVDV 2, and a plurality of antigenic sites derived from two or more of the BVDV 1 or BVDV 2 proteins selected from the group consisting of capsid, $E^{ms}$, E1, E2, NS2 and NS3; and
   b) administering said vaccine to said subject under conditions such that protective immunity is induced.

2. The method of claim 1, wherein said subject is a bovine.

3. The method of claim 1, wherein said subject is a neonatal calf.

4. The method of claim 1, wherein said subject has neutralizing antibodies for said virus vaccine particle prior to said administering of said vaccine.

5. The method of claim 4, wherein said neutralizing antibodies are maternal antibodies.

6. The method of claim 4, wherein said neutralizing antibodies are BVDV 1-specific antibodies.

7. The method of claim 4, wherein said neutralizing antibodies are BVDV 2-specific antibodies.

8. The method of claim 4, wherein said vaccine evades said neutralizing antibodies.

9. The method of claim 1, wherein each of said plurality of antigenic sites is masked by one of a plurality of bi-specific diabodies, wherein each of said plurality of bi-specific diabodies comprise a viral antigen binding moiety.

10. The method of claim 9, wherein said at least one of said plurality of bi-specific diabodies further comprises a cell surface antigen binding moiety fused in-frame with said viral antigen binding moiety.

11. The method of claim 10, wherein said cell surface antigen binding moiety binds to a dendritic cell.

12. The method of claim 11, wherein said bound cell surface antigen binding moiety activates said dendritic cell.

13. The method of claim 11, wherein said bound cell surface antigen binding moiety recruits said dendritic cell.

14. The method of claim 10, wherein said cell surface antigen binding moiety is a dendritic cell surface antigen binding moiety.

15. The method of claim 14, wherein said dendritic cell surface antigen binding moiety is a bovine CD205 antigen receptor binding moiety.

16. The method of claim 9, wherein said viral antigen binding moiety binds to at least one of said plurality of antigenic sites.

17. The method of claim 1, wherein said vaccine is a bovine viral diarrhea virus 1 vaccine.

18. The method of claim 1, wherein said vaccine is a bovine viral diarrhea virus 2 vaccine.

19. The method of claim 1, wherein said vaccine is a mixture of a bovine viral diarrhea virus 1 vaccine and a bovine viral diarrhea virus 2 vaccine.

20. The method of claim 1, wherein said vaccine is a live vaccine.

21. The method of claim 20, wherein said live vaccine is a modified live vaccine.

22. The method of claim 1, wherein said vaccine further comprises a recombinant adenovirus that expresses Flt3L, GM-CSF and CD40L.

23. The method of claim 1, wherein said plurality of antigenic sites further comprises a protein fragment derived from a virus selected from the group consisting of bovine respiratory viruses, bovine respiratory syncytial virus, infectious bovine rhinotracheitis, bovine parainfluenza-3 virus, bovine herpes virus 1 and bovine herpes virus 2.

* * * * *

SEQUENCE LISTING

```
<160> NUMBER OF SEQ ID NOS: 12

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Asp Tyr Lys Asp Asp Asp Asp Lys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Gly Gly Gly Gly Ser
1               5
```

```
<210> SEQ ID NO 3
<211> LENGTH: 20
<212> TYPE: PRT
<213> ORGANISM: Artificial Sequence
<220> FEATURE:
<223> OTHER INFORMATION: Synthetic

<400> SEQUENCE: 3

Gly Gly Gly Gly Ser Gly Gly Arg Ala Ser Gly Gly Gly Gly Ser Gly
1               5                   10                  15

Gly Gly Gly Ser
            20

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Cys Cys Cys Cys Ser
1               5

<210> SEQ ID NO 6
<211> LENGTH: 18
<212> TYPE: PRT
<213> ORGANISM: Artificial Sequence
<220> FEATURE:
<223> OTHER INFORMATION: Synthetic

<400> SEQUENCE: 6

Gln Gly Gly Ile Ser Ser Val Asp His Val Thr Ala Gly Lys Asp Leu
1               5                   10                  15

Leu Val

<210> SEQ ID NO 7
<211> LENGTH: 18
<212> TYPE: PRT
<213> ORGANISM: Artificial Sequence
<220> FEATURE:
<223> OTHER INFORMATION: Synthetic

<400> SEQUENCE: 7

Val Thr Ala Ser Gly Thr Pro Ala Phe Phe Asp Leu Lys Asn Leu Lys
1               5                   10                  15

Gly Trp

<210> SEQ ID NO 8
<211> LENGTH: 18
<212> TYPE: PRT
<213> ORGANISM: Artificial Sequence
<220> FEATURE:
<223> OTHER INFORMATION: Synthetic
```

```
<400> SEQUENCE: 8

Val Glu Tyr Ser Tyr Ile Phe Leu Asp Glu Tyr His Cys Ala Thr Pro
1               5                   10                  15

Glu Gln

<210> SEQ ID NO 9
<211> LENGTH: 18
<212> TYPE: PRT
<213> ORGANISM: Artificial Sequence
<220> FEATURE:
<223> OTHER INFORMATION: Synthetic

<400> SEQUENCE: 9

Cys Ala Thr Pro Glu Gln Leu Ala Ile Ile Gly Lys Ile His Arg Phe
1               5                   10                  15

Ser Glu

<210> SEQ ID NO 10
<211> LENGTH: 18
<212> TYPE: PRT
<213> ORGANISM: Artificial Sequence
<220> FEATURE:
<223> OTHER INFORMATION: Synthetic

<400> SEQUENCE: 10

Met Lys Gly Asn Met Leu Val Phe Val Pro Thr Arg Asn Met Ala Val
1               5                   10                  15

Glu Val

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Gly Arg Val Lys Pro Gly Arg Tyr Tyr Arg Ser Gln Glu Thr Ala
1               5                   10                  15

<210> SEQ ID NO 12
<211> LENGTH: 18
<212> TYPE: PRT
<213> ORGANISM: Artificial Sequence
<220> FEATURE:
<223> OTHER INFORMATION: Synthetic

<400> SEQUENCE: 12

Asn Gly Glu Val Thr Asp Thr Tyr Glu Asn Tyr Ser Phe Leu Asn Ala
1               5                   10                  15

Arg Lys
```